US009636397B2

(12) United States Patent
Miller et al.

(10) Patent No.: US 9,636,397 B2
(45) Date of Patent: May 2, 2017

(54) ADJUVANT COMPOSITIONS AND RELATED METHODS

(71) Applicant: VaxLiant, LLC, Lincoln, NE (US)

(72) Inventors: Timothy J Miller, Lincoln, NE (US); Mary Ann Pfannenstiel, Lincoln, NE (US)

(73) Assignee: Vaxliant, LLC, Lincoln, NE (US)

( * ) Notice: Subject to any disclaimer, the term of this patent is extended or adjusted under 35 U.S.C. 154(b) by 0 days.

(21) Appl. No.: 15/079,936

(22) Filed: Mar. 24, 2016

(65) Prior Publication Data

US 2016/0279237 A1 Sep. 29, 2016

Related U.S. Application Data

(60) Provisional application No. 62/137,659, filed on Mar. 24, 2015.

(51) Int. Cl.

| | |
|---|---|
| ***A61K 45/00*** | (2006.01) |
| ***A61K 47/00*** | (2006.01) |
| ***A61K 49/00*** | (2006.01) |
| ***A61K 39/39*** | (2006.01) |
| ***A61K 39/108*** | (2006.01) |
| ***A61K 39/145*** | (2006.01) |
| *A61K 39/00* | (2006.01) |

(52) U.S. Cl.

CPC .......... *A61K 39/39* (2013.01); *A61K 39/0258* (2013.01); *A61K 39/145* (2013.01); *A61K 2039/521* (2013.01); *A61K 2039/53* (2013.01); *A61K 2039/55511* (2013.01); *A61K 2039/55577* (2013.01); *C12N 2760/16134* (2013.01)

(58) Field of Classification Search

CPC ..................................................... A61K 39/00

USPC ....................................... 424/9.1, 9.2, 278.1

See application file for complete search history.

(56) References Cited

U.S. PATENT DOCUMENTS

2008/0292663 A1* 11/2008 Gerber ................ A61K 9/0019 424/280.1

FOREIGN PATENT DOCUMENTS

WO WO2009/156960 A2 * 12/2009 ............ A61K 39/00

* cited by examiner

*Primary Examiner* — Rodney P Swartz

(74) *Attorney, Agent, or Firm* — Tracey S. Truitt; Kelley Schneiders; Polsinelli PC

(57) ABSTRACT

The present disclosure provides for an adjuvant composition that is suited for injectable as well as transdermal administration. The adjuvant composition generally comprises a lipophile, a polymer of acrylic or methacrylic acid, saline, cholesterol, a saponin, and sodium hydroxide. A vaccine composition is also provided for that generally includes the vaccine composition of the present disclosure and a DNA component. A method for vaccinating animals and humans utilizing the adjuvant composition of the present disclosure is also provided.

11 Claims, 2 Drawing Sheets

Plasmid DNA Poultry Adjuvant 01
18 Months (storage at 2-7°C)

| Lane | Sample | DNA Concentration |
|---|---|---|
| 1 | 1kb ladder | N/A |
| 2 | Super Coiled ladder | N/A |
| 3 | Plasmid DNA Stock | 400ng |
| 4 | | 200ng |
| 5 | | 100ng |
| 6 | ENABL™ 1 + DNA | 400ng |
| 7 | | 200ng |
| 8 | | 100ng |
| 9 | Buffer + DNA | 400ng |
| 10 | | 200ng |
| 11 | | 100ng |
| 12-17 | Other samples | Not Shown |
| 18 | No Template Control | N/A |
| 19-20 | Empty | Not Shown |

ADJUVANT COMPOSITIONS AND RELATED METHODS

SEQUENCE LISTING

This application contains a sequence listing in paper format and in computer readable format, the teachings and content of which are hereby incorporated by reference.

FIELD OF DISCLOSURE

The field of disclosure relates to adjuvant compositions for use in bio-pharmaceutical preparations. The adjuvants are particularly suited to use with bio-pharmaceutical preparations that include a purified DNA component, such as non-replicative or replicative DNA in mammalian cells or tissue.

BACKGROUND

Adjuvants have the potential to impact or even determine the success or failure of vaccine compositions. Additionally, adjuvants often determine or augment the administration method of a given antigen. Further, in the area of DNA and gene vaccines used for therapeutic or prophylactic purposes it is thought that the use of Ca++ and divalent cations are required for efficacy when making a DNA vaccine. The Ca++ and divalent cations are often added to or formed as a derivative of liposomal delivery vehicles that are unstable when suspended in aqueous (water) solutions. These steps and production of these materials are time consuming and add to the cost of vaccine manufacturing. It is known in the art that DNA vaccines require multiple doses in order to elicit an immune response that protects the recipient against a challenge. Further, DNA vaccines require high doses of DNA ranging from a few hundred micrograms to milligrams of purified DNA per dose.

All routes of vaccine administration could benefit from enhanced efficacy and controlled formulation including the ability to use less antigen to receive the same or better immunogenic response. What is needed in the art are adjuvant compositions that can be formulated to suit DNA vaccines that do not require the use of cations or liposomal delivery vehicles. Further, adjuvant formulations are needed that provide an efficacious vaccine after a single dose of the vaccine. Such compositions place less stress on the recipient and are more cost-effective. Finally, compositions with improved capability such as onset and duration of immunity are also needed in the art. Compositions that can be delivered by multiple routes of inoculation such as intravenous, subcutaneous, intramuscular, transdermal, oral, and mucosal are also needed in the art.

SUMMARY OF DISCLOSURE

The present disclosure overcomes the problems inherent in the prior art and provides for adjuvant compositions and vaccine compositions suitable for use in animals such as birds and mammals including humans. The present disclosure additionally provides for methods related to such adjuvant and vaccine compositions. The adjuvant compositions of the present disclosure are especially suited for use with pharmaceutical preparations which include DNA and other related genetic material. The vaccines of the present disclosure incorporating DNA have been surprisingly found to require less DNA than in previous vaccine formulations and can be made without the use of Ca++, divalent cations, or divalent cation derived liposomal vehicles. Further, the vaccine compositions of the present disclosure incorporating the adjuvants of the present disclosure have the unexpected benefit of inducing an immune response that would protect the recipient from challenge after a single dose administration of the vaccine composition, with lower doses of DNA. These features represent advancement in the art and a benefit to the recipient.

The adjuvant compositions of the present disclosure are particularly suited for use in connection with DNA based vaccines or immunogenic compositions. A DNA based vaccine or immunogenic composition is any composition capable of inducing an immune response having DNA as the antigenic portion of the composition. For purposes of the present disclosure, DNA can be referred to as "the backbone DNA", however the present disclosure is not so limited. In some embodiments the DNA backbone is non-replicating (killed), preferably highly purified, double stranded, circular, covalently closed, supercoiled DNA. In other embodiments, the DNA backbone is replicative. The backbone DNA can comprise a feature selected from, but not limited to, a multiple cloning sites for insertion of a foreign gene, a eukaryote-specific promoter motif that is only activated in mammalian cells, a poly A-addition site, or any combination thereof. In a further embodiment, the non-replicative DNA can be amplified in bacterial fermentation, such as that derived by *Escherichia coli* (*E. coli*) through use of a selectable marker gene that allows selection of host cells retaining the plasmid DNA and a high copy replication competent motif for high copy production in bacteria. In yet another embodiment, the DNA backbone is suited to accept different types of gene inserts for expression in mammalian cells. In a further embodiment, the DNA-based vaccine is capable of encoding the entire complement of genes needed for replication of virus particles, virus-like particles, or virus vectors, utilized for vaccination or gene therapy in mammalian cells or tissue. In an additional embodiment, the DNA component of a vaccine or immunogenic composition of the present disclosure is competent for replication in mammalian cells and contains one or more motifs, selected from, but not limited to, motifs for initiation of DNA replication in mammalian cells, motifs for transcription initiation and termination of genes in mammalian cells, gene motifs for production of encapsulation or packaging of the genetic material derived from the replication competent DNA from mammalian cells, and combinations thereof.

In one embodiment, the present disclosure provides for an improved efficient delivery of DNA-based vaccines or immunogenic compositions, which also results in a greater immune response in the recipient, when compared to previous DNA-based vaccines. Further, it allows for a more rapid response time to evolving diseases, meaning that vaccines or immunogenic compositions can be developed more rapidly in response to outbreaks of new pathogens. Using the adjuvants of the present disclosure provides for a method where a gene can be isolated from a tissue isolated from an infected animal (including humans) and can be amplified within hours after the tissue is prepared, with the gene sequence isolated and the gene sequence evaluated in matter of a few days. Therefore, using the adjuvants of the present disclosure, the new gene can be deposited directly into a DNA-based vaccine backbone and a new vaccine can be made ready in a matter of days, rather than months or years by conventional technology. Thus, the adjuvants of the present disclosure provide a way to meet the evolving disease issue in both humans and animals, that is both expeditious in reaching manufacturing license approval by regulatory authorities, is cost effective for manufacturing, and efficacious to the recipient. A further advantage is that a single dose of a vaccine comprising the adjuvant compositions of the present disclosure is required for efficacy against challenge. However, multiple doses may be administered, where two, three, four, and five doses are envisioned.

The adjuvant compositions of the present disclosure generally include the use of a lipophile, where the lipophile is preferably selected from a composition commercially known as Labrafac™ (Gattefossé, Lyon, France) or lecithin. The efficacy of the vaccines of the present disclosure, incorporating adjuvants of the present disclosure, does not depend on the addition or absence of lecithin. However, adjuvants including lecithin are generally more suited for, but not limited to, administration routes that require injection, while the adjuvant compositions incorporating Labrafac™ are generally more suited for, but not limited to, administration routes that require injection as well as needleless administration methods.

The adjuvant compositions of the present disclosure preferably provide for 0.1% to 20% higher absorption of antigen to the composition such that when administered there is a more efficacious immune response. Thus, a lower amount of antigen can be used to induce the required level of an immune response. More preferably, the absorption or reaction is about 1% to 20% higher, where ranges and values such as 1% to 15%, 5% to 20%, 1% to 18%, 2% to 18%, 0.5%, 3%, 4%, 5%, 6%, 7%, 8%, 9%, 10%, 11%, 12%, 13%, 14%, 15%, 16%, 17%, 18%, and 19% are envisioned.

When combined with an antigen such as in a vaccine or immunogenic composition, the adjuvant compositions of the present disclosure provide improved presentation of the antigen portion of the vaccine to the immune system of the recipient of the vaccine, when compared to previous vaccines or immunogenic compositions comprising adjuvants not provided in the present disclosure. Such improved presentation is in comparison to the same antigen when combined with an adjuvant composition that is not part of this disclosure. Preferably, the improved presentation permits the use of smaller or lower amounts of antigen to achieve the same level of immune system reaction. The level of immune system reaction can be measured by the strength of the response, as measured by markers of immune response, or can be measured by the duration of immunity, or combinations of these two indicators of immune system reaction. Even more preferably, the improved antigen presentation permits the use of 95% of the amount of antigen, more preferably 90%, still more preferably 85%, 80%, 75%, 60%, 65%, 60%, 55%, 50%, 45%, 40%, 35%, 30%, 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009, 0.008%, 0.007%, 0.006%, 0.005%, as well as ranges formed by any two members of this group, to achieve the same level of immune system reaction as the same antigen in combination with a different adjuvant when administered to an animal of the same species.

A further advantage of the adjuvant compositions of the present disclosure and related methods are that some embodiments do not include lecithin as lecithin has been shown not to be useful for all antigen types. The adjuvant composition of the present disclosure preferably provides effective adjuvant compositions and related methods which do not utilize lecithin and have been shown to provide enhanced immune response for antigens that lecithin does not induce or provide an immune response against.

The adjuvant composition of the present disclosure generally comprises a lipophile, a polymer of acrylic or methacrylic acid, saline, cholesterol, alcohol, a saponin, and sodium hydroxide. The adjuvant composition has been shown to work for needleless administration, dermal administration, and other routes of administration.

Advantageously, the adjuvant composition of the present disclosure has low virucidal and cytotoxic effect on the antigen, meaning that the adjuvant composition does not degrade the antigen, making it ineffective to induce an appropriate immune response in a recipient. For the same reason when the adjuvant is combined to the antigen the resulting composition can be used to screen the immune response in vitro. Preferably, the virucidal activity of the adjuvant has a tissue culture EID50 when the lipid concentration is less than 5% lipid. Cytotoxic effects on cell culture varies depending on the cell culture used, but a safe range can be from 0.025% to 5%. Preferred ranges are less than 5%, more preferably less than 4%, still more preferably between 0.25% to about 3%, and even more preferably between about 0.25% and 2%.

The adjuvant composition of the present disclosure is preferably shelf stable for at least 6 months, more preferably at least 12 months, still more preferably at least 18 months, and even more preferably at least 24 months or longer when made in liquid form at room temperature (about 60-75° C.) or when stored at refrigerated temperatures (2° C. to 7° C.). The adjuvant can also be frozen and stored at −18 to −22° C., or −40 to −80° C. The adjuvants can also be freeze dried and stored at (2° C. to 7° C.), making the use of the adjuvants highly versatile for use with vaccines and biological materials.

The present disclosure further provides for a vaccine or immunogenic composition comprising the adjuvant composition of the present disclosure and an antigen. The antigen can be any antigen suitable for use as an immunogenic composition or vaccine. In a preferred embodiment, the antigen is DNA, which includes a replicative competent DNA or a non-replicative competent DNA. Preferably, the non-replicative competent DNA in the form of a covalently closed circular supercoiled plasmid or synthetically derived DNA. Preferably, the ratio of the adjuvant of the present disclosure to the antigen is between about 1:20 and 1:1, more preferably about 1:20, 1:17, 1:15, 1:12, 1:10, 1:9, 1:8, 1:7, 1:6, 1:5, 1:4, 1:3, 1:2, and 1:1.5, with 1:5 being particularly preferred.

The vaccine of the present disclosure preferably comprises the adjuvant formulation of the present disclosure and a DNA component. Most preferably, where the antigen can be a non-replicative or replicative competent DNA in the form of a plasmid. The art surrounding DNA-based vaccines provides that Ca++ is required for effective delivery of the DNA component of the vaccine, where cationic systems are prevalent in the art. The vaccine of the present disclosure is surprisingly effective without the use of Ca++ or cations representing an advancement in the art. In a further embodiment, the vaccine of the present disclosure requires only a small amount of DNA. Preferably, the DNA is present in an amount of from about 250 μg to 0.25 μg per dose, where ranges and values such as 100 to 250 μg, 25 to 50 μg, 30 to 60 μg, 1 to 30 μg, 0.25 to 25 μg, 0.3 μg, 0.5 μg, 0.75 μg, 1 μg, 1.25 μg, 5 μg, 10 μg, 12 μg, 15 μg, 17 μg, 20 μg, 22 μg, 25 μg, 27 μg, 30 μg, 35 μg, 55 μg, 60 μg, 80 μg, 90 μg, 110 μg, 150 μg, 200 μg, and 225 μg are envisioned. This is preferably at least 30% less, more preferably at least 50% less, still more preferably at least 90% less, more preferably at least 40% less, more preferably at least 75% less, more preferably at least 90% less than the amount of DNA used in commercially available DNA-based vaccines, where values such as 40% less, 45% less, 55% less, 60% less, 70% less, 95% less, and 98% less are envisioned. In a preferred embodiment, the amount of DNA is determined per dose of vaccine.

A single dose vaccine is also provided by the present disclosure. The single dose vaccine comprises the adjuvant formulation of the present disclosure and at least one DNA component. The DNA component is preferably selected from the group consisting of non-replicative competent and replicative competent that is incorporated into a double stranded DNA complex that can be linear, relaxed circular or circular covalently closed super coiled DNA derived from plasmid DNA from bacterial fermentation, or by DNA synthesis. The single dose vaccine composition is effective at inducing an immune response which reduces the severity of or incidence of clinical signs of infection in an animal after a single dose. For purposes of the present disclosure, a single dose means that only 1 administration of the vaccine is provided to the animal. Preferably, the single dose vaccine of the present disclosure is formulation without Ca++, without liposome delivery, and with low dose of DNA.

The vaccine composition or immunogenic composition of the present disclosure, whether provided in a single dose or multiple doses, is preferably shelf stable for at least 6 months, more preferably at least 12 months, still more preferably at least 18 months, and most preferably at least 24 months or longer. Preferably, when the vaccine of the present disclosure incorporates a protein, the vaccine composition is stable for at least 12 months. In an embodiment, where the vaccine of the present disclosure includes a DNA component, the vaccine is stable for at least 12 months, more preferably, at least 18 months, and most preferably, at least 24 months or longer.

A method of vaccinating an animal or human is also provided. The steps of the method preferably include administering the vaccine composition of the present disclosure to a recipient in need thereof. The vaccine can be administered via needleless administration or injected, where injected administration methods include, but are not limited to, subcutaneous injection, intramuscular injection, intradermal, and intravenous routes of inoculation. The recipient is preferably a human or animal, where the animal is selected from, but is not limited to, birds, cows, pigs, horses, dogs, cats, mules, sheep, monkeys, companion animals and other mammals. In one embodiment, the vaccine composition is administered a single time. Needleless administration methods include, but are not limited to, vaccine guns, transdermal patches, aerosols, mucosal administration methods, skin adhesion methods, dry particle projectiles, wet projectiles, gold/inert particle guns, pneumatic guns, mucosal, and oral routes of inoculation.

A vaccine or immunogenic composition suited for pigs is also provided by the present disclosure, where the vaccine comprises an adjuvant of the present disclosure incorporating Labrafac™ and DNA, where the DNA may be replicative competent or non-replicative competent. The vaccine suited for pigs is preferably administered via transdermal administration, where a vaccine gun can be used, although this is not required.

All reference to "comprises" or "comprising" in the present disclosure shall also provide the basis for a "consisting essentially of" or "consisting of" claim language. For example, if the present disclosure provides that the composition comprises A and B, it is understood that the composition can also consist essentially of A and B, or even consist of A and B and each of these are fully disclosed as if they were specifically written for each portion of the disclosure. Each of these terms shall be accorded their usual meaning when used in the preamble of a claim.

DETAILED DESCRIPTION

Figure 1:
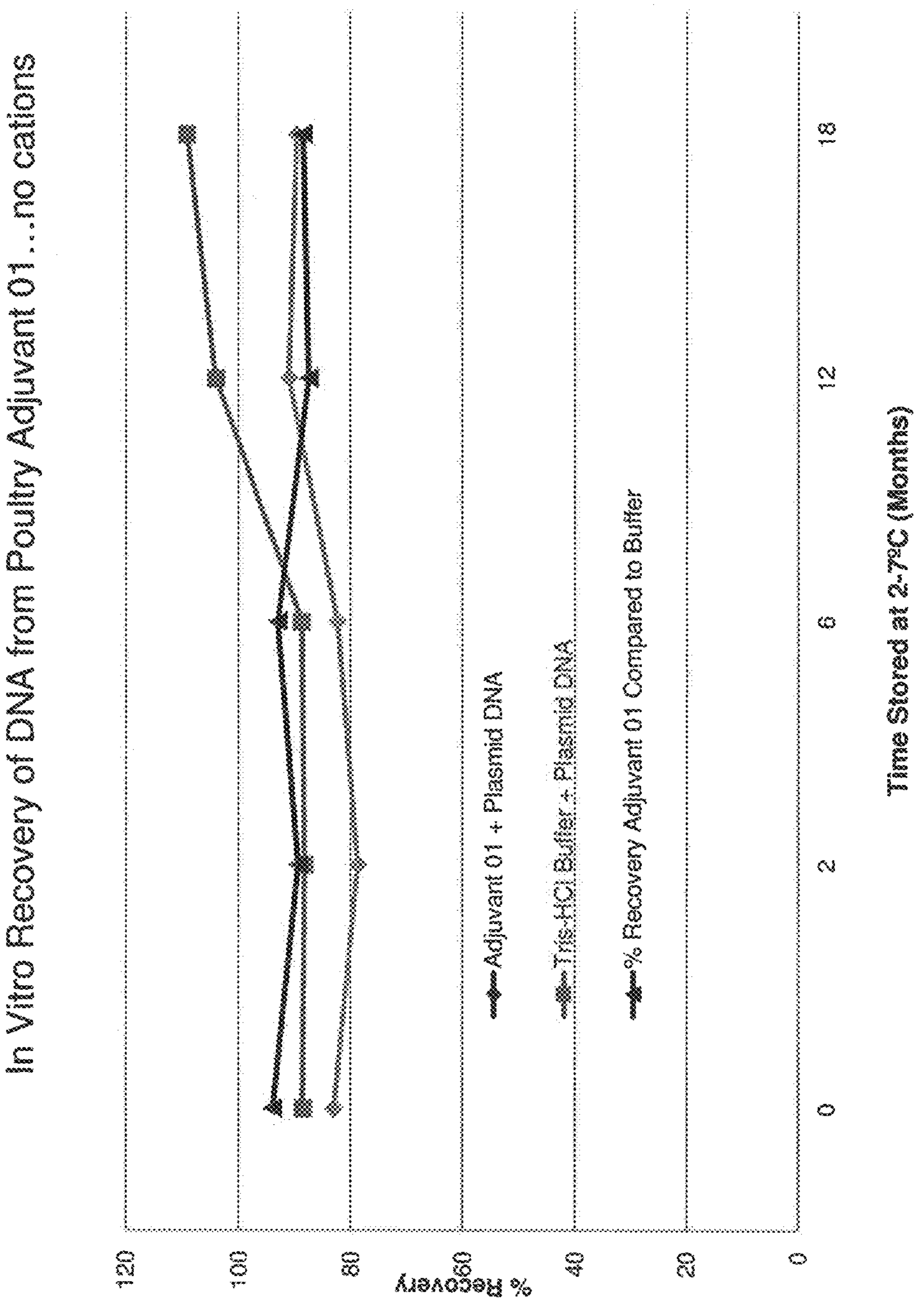
FIG. 1 is a graphical representation of the percent recovery of double stranded covalently closed DNA from buffer and from adjuvant with respect to time from Example 7.

The adjuvant composition of the present disclosure preferably comprises a lipophile and a polymer of acrylic or methacrylic acid or any particle type component. In other embodiments, the adjuvant composition further comprises at least one of the following: saline, immunomodulators, small molecules, cytokines, sterols including cholesterol, alcohol, a saponin, and sodium hydroxide.

The lipophile can be any lipophile with having medium chain triglycerides. Preferably, the lipophile is selected from the group consisting of medium chain EP triglycerides, medium chain triglycerides NF, medium chain fatty acid triglyceride JPE, caprylic/capric triglyceride, and combinations thereof. In a preferred embodiment, the lipophile is Labrafac™ (Gattefossé, Lyon, France). In an alternate embodiment, the lipophile is lecithin.

In a preferred embodiment, the lipophile is present in the adjuvant composition of the present disclosure in an amount of from about 0.01% to about 5% of the total volume of the composition, where amounts including 0.1% to 4.7%, 0.2% to 4.5%, 0.3 to 4.4%, 0.5% to 4.3%, 0.7% to 4.2%, 0.9% to 4.1%, 1% to 4%, 2% to 4%, 2% to 5%, 0.1% to 0.5%, 0.1% to 0.8%, 0.1% to 1%, 0.3% to 1.5%, 0.3% to 1.5%, 3% to 5%, 0.1%, 0.2%, 0.3%, 0.4%, 0.5%, 0.6%, 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, 3.0%, 3.2%, 3.4%, 3.5%, 3.8%, 4%, 4.2%, 4.5%, 4.8%, and 5% by volume and all ranges from any two points there between are envisioned. In a most preferred embodiment, the lipophile is present in an amount of about 0.4% by volume.

The polymer of acrylic or methacrylic acid compound is preferably selected from the polymers of acrylic or methacrylic acid and the copolymers of maleic anhydride and alkenyl derivative. Examples of such compounds include the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol™; (BF Goodrich, Ohio, USA) are particularly appropriate. They are cross-linked with an allyl sucrose or with allyl pentaerythritol. There are a variety of Carbopol™ products which would be suitable for use with the present disclosure. Most preferred is the use of Carbopol™ 974P NF Polymer.

In a preferred embodiment, the polymer of acrylic or methacrylic acid is preferably present in the adjuvant composition of the present disclosure in an amount of from about 0.025% to about 3.0% by volume, where values such as 0.025% to 1%, 0.05% to 0.15%, 0.1% to 0.2%, 0.1% to 1.5%, 0.5% to 1%, 0.5% to 2%, 0.5% to 3%, 0.2%, 0.3%, 0.4%, 0.5%, 0.6%. 0.7%, 0.8%, 0.9%, 0.94%, 0.95%, 0.96%, 0.97%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. In a most preferred embodiment, the polymer of acrylic or methacrylic acid is present in an amount of about 0.2% by volume.

The saline component can be any solution of sodium chloride and water suitable for use in an adjuvant composition. Typically, saline refers to a solution of 0.90% w/v of NaCl, about 300 mOsm/L or 9.0 g per liter, however, saline for purpose of the present disclosure is not limited to this solution. In a most preferred embodiment, the saline solution is Dulbecco's Phosphate Buffered Saline without Calcium or Magnesium (Cellgro Catalog No. 21-CV).

In a preferred embodiment, the saline solution is present in an amount of from about 50% to 98% of the adjuvant composition of the present disclosure by volume, where amounts such as 60% to 98%, 70% to 98%, 80% to 98%, 90% to 98%, 50% to 60%, 55% to 75%, 63% to 91%, 55%, 60%, 65%, 70%, 75%, 80%, 85%, 86%, 87%, 88%, 89%, 90%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 94%, 95%, 96%, 97%, and 98% are envisioned. In a most preferred embodiment, saline is present in the adjuvant composition of the present disclosure in an amount of about 92% by volume.

The alcohol component is preferably selected from the group consisting of ethanol, isopropanol, butanol, and combinations thereof. In a preferred embodiment, ethanol is used. Preferably, the ethanol is a 90% to 100% solution, however, ethanol solutions from 10% to 90% could also be utilized for purposes of the present disclosure.

In a preferred embodiment, the alcohol is present in an amount of from about 0.01% to 3% of the adjuvant composition of the present disclosure, by volume, where values such as 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.6%. 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. Further, ranges incorporating any two of the described values are also envisioned. For example, 0.01% to 1%, 0.01% to 2%, 0.3% to 1%, 0.3% to 1.5%, 0.03% to 0.07%, 0.05% to 2.4%, and 1% to 1.6% are all covered by the present disclosure. In a most preferred embodiment, the alcohol is present in the adjuvant composition of the present disclosure in an amount of about 0.05% by volume. The alcohol is useful for solubilizing the saponin, preferably Quil A and much or most (at least 10%, 20%, 30%, 40%, 50%, 60%, 70%, or more) dries off leaving the final concentration of the alcohol in the final product very low.

The saponin for purposes of the present disclosure can be any selected from the class of saponins. Generally, saponins are a class of chemical compounds found in particular abundance in various plant species. Preferably, they are amphipathic glycosides grouped phenomenologically by the soap-like foaming they produce when shaken in aqueous solutions, and structurally by having one or more hydrophilic glycoside moieties combined with a lipophilic triterpene derivative. In a preferred embodiment, the saponin is purified or semi-purified and lyophilized. Preferably, the saponin is an extract from the cortex of the South American tree, *Quillaja saponaria* Molia. Most preferably, the saponin is Quil A.

In a preferred embodiment, the saponin is present in the adjuvant composition of the present disclosure in an amount of about 0.0001% to about 0.5%, where values such as 0.0001%, 0.0002%, 0.0005%, 0.0007%, 0.0008%, 0.00085%. 0.0009%, 0.00095%, 0.00099%, 0.001%, 0.002%, 0.003%, 0.004%, 0.005%, 0.006%. 0.007%, 0.008%, 0.009%, 0.01%, 0.015%, 0.02%, 0.025%, 0.03%, 0.035%, 0.04%, 0.045%, 0.05%, 0.06%, 0.07%, 0.08%, 0.09%, 0.1%, 0.15%, 0.2%, 0.25%, 0.3%, 0.35%, 0.4%, 0.45% and 0.5% are envisioned. Further, ranges including any two discreet values described above are also envisioned. For example, the saponin may be present in the adjuvant composition of the present disclosure in an amount from about % to 0.003%, 0.003% to 0.01%, 0.003% to 0.05%, 0.01% to 0.03%, 0.1%, to 0.5%, 0.07% to 0.2%, and the like. In a most preferred embodiment, the saponin is present in an amount of about 0.002%.

The adjuvant composition of the present disclosure preferably includes a sterol. Any sterol will work for purposes of the present disclosure, including those that occur in plants, animals, and fungi. The sterol is preferably taken from a plant source, however, the sterol may be selected from but not limited to, phytosterols, zoosterols, cholesterol, campesterol, sitosterol, stigmasterol, grgosterol, and combinations thereof. In a most preferred embodiment, the sterol is a phytosterol, more preferably cholesterol, preferably of non-animal origin. The cholesterol can be any cholesterol source suitable for use in an adjuvant composition. The cholesterol is preferably derived from animals or plants, most preferably, the cholesterol is plant derived.

In a preferred embodiment, the cholesterol is present in the adjuvant composition of the present disclosure in an amount of from about 0.0001% to about 3% by volume, where values such as 0.0001% to 0.005%, 0.0005% to 1%, 0.0008% to 0.008%, 0.002%, 0.003%, 0.004%, 0.005%, 0.006%. 0.007%, 0.008%, 0.009%, 0.01%, 0.02%, 0.03%, 0.04%, 0.05%, 0.06%. 0.07%, 0.08%, 0.09%, 0.1%, 0.2%, 0.3%, 0.4%, 0.5%, 0.6%. 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. Further, ranges including any two of these volumes are also envisioned. In a most preferred embodiment, the cholesterol is present in an amount of about 0.002% by volume.

The adjuvant composition of the present disclosure preferably comprises a component that neutralizes the pH of the composition to a pH from about 6-8, more preferably to a pH of 7. Any conventional neutralizer can be use, but preferably, the neutralizer is selected from the group consisting of sodium hydroxide, potassium hydroxide, and ammonium hydroxide. In a most preferred embodiment, the component that neutralizes the pH of the solution is sodium hydroxide.

In a preferred embodiment, the component that neutralizes the pH of the adjuvant composition is present in an amount of about 0.1% to 10%, where values such as 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, and 10% are envisioned. Additionally, any range incorporating two of these values is also envisioned including, but not limited to 2% to 8%, 2% to 6%, 3% to 8%, 4% to 6%, 1.5%, 2%, 2.5%, 3%, 3.5%, 4%, 4.5%, 5%, 5.5%, 6%, 6.5%, 7%, 7.5%, 8%, 8.5%, 9%, and 9.5% are envisioned. In a most preferred embodiment, the component that neutralizes the pH of the adjuvant composition is present in an amount of about 5% by volume.

In another embodiment of the present disclosure, the adjuvant composition comprises Labrafac™, cholesterol, and Quil-A. In an additional embodiment, the adjuvant composition of the present disclosure comprises Labrafac™, Carbopol™, Saline, Cholesterol, Ethanol, Quil-A and Sodium Hydroxide. In yet a further embodiment, the adjuvant composition of the present disclosure comprises Labrafac™, Carbopol™ 974 P, Saline, vegetable-derived Cholesterol, Ethanol, Quil-A, and Sodium hydroxide. In another embodiment, the adjuvant composition of the present disclosure comprises about 0.04% Labrafac™, by volume, about 0.2% Carbopol™, by volume, about 92% Saline, by volume, about 0.002% Cholesterol, by volume, about 0.5% Ethanol, by volume, about 0.002% Quil-A, by volume, and about 1% Sodium hydroxide. In one embodiment, the rest of the composition is water. In another embodiment, the adjuvant composition of the present disclosure comprises about 2.0% Labrafac™, by volume, about 1.0% Carbopol™, by volume, about 92% Saline, by volume, about 0.002% Cholesterol, by volume, about 0.5% Ethanol, by volume, about 0.01% Quil-A, by volume, and about 1% Sodium hydroxide. In other embodiments, lecithin is substituted for Labrafac™.

In one embodiment, the adjuvant composition of the present disclosure forms emulsions that preferably form particles that are 10 nm to 2000 nm in diameter as measured by microscopy or by particle counters. Preferably the particle size should be 80 nm to 500 nm to allow processing by antigen presenting cells in the recipient.

The adjuvant composition of the present disclosure is preferably shelf stable for at least 6 months, more preferably at least 12 months, still more preferably at least 18 months, and even more preferably at least 24 months or longer. The stability preferably refers to the ability to keep biophysical and efficacy features after incubation for long periods of time at either room temperature (about 60° F. to 80° F., about 18° C. to 26° C.) and in refrigerated temperatures (2° C. to 7° C.). The adjuvant composition of the present disclosure can also be frozen (−18° C. to −22° C.; −40° C. to −85° C. or freeze dried and stored at refrigerated temperatures (2° C. to 7° C.) and when resuspended after being freeze dried.

The present disclosure also provides for a vaccine composition or immunogenic composition. The vaccine or immunogenic composition preferably comprises the adjuvant composition of the present disclosure and an antigen(s). Preferably, the antigen(s) are DNA, where the DNA may be incorporated into a plasmid, provided as replication competent DNA, and/or non-replication competent DNA. A replicative competent DNA is described as a DNA that can be in the form of double covalently closed circular supercoiled (dsCCSC) DNA, double stranded linear DNA (dsL), or double stranded relaxed circular (dsRC) DNA that encodes the gene sequence motifs that allow the DNA replication complexes of mammalian cells to amplify and replicate the DNA being delivered to the cell by the delivery vehicle. Replication competent DNA can also contain the entire coding region for virus vector and virus-like particles to be formed.

Non-replication competent DNA include double covalently closed circular supercoiled (dsCCSC) DNA, double stranded linear DNA (dsL), or double stranded relaxed circular (dsRC) DNA that cannot be replicated in mammalian cells. An example of non-replicative DNA is by way of the RIG-I DNA vaccines described by Nature Technology Corporation (NTC)[1]. The NTC DNA vaccines include a retinoic acid inducible gene-1 (RIG-I) activating DNA sequence and are advanced vectors for improved DNA vaccination. The RIG-I DNA of the disclosure include motifs to increase DNA vaccine induced innate immune responses and improve adaptive immunity for vaccination in large animals and humans. Retinoic-acid-inducible gene 1 (RIG-I) is a critical cytoplasmic double stranded RNA (dsRNA) pattern receptors required for innate immune activation in response to viral infection. Activation of RIG-I leads to type I interferon (IFN) and cytokine production through interferon-β promoter stimulator 1 (IPS-1) signaling. NTC has developed optimized, potent plasmid encoded RNA polymerase III expressed RNA-based RIG-I agonists (eRNAs) (e.g. eRNA41H) which are integrated into the backbone of DNA vaccine vectors. Combinational RIG-I agonist eRNA41H (eRNA11a and Adenoviral RNA VAI) activates an IFNβ reporter in human (HEK293 and A549) and murine (NIH3T3 and L929) cell lines (Luke et al. 2011a). These plasmids are dsCCSC DNA and are specifically designed as safe minimalized antibiotic-free selection vectors for the expression of recombinant proteins in mammalian cells.

[1] Luke J, Carnes A E, Hodgson C P, and Williams J A. (2009) Improved antibiotic-free DNA vaccine vectors utilizing a novel RNA based plasmid selection system. Vaccine 27: 6454-6559

Luke J, Simon G G, Soderholm J, Errett J S, August J T, Gale M Jr., Hodgson C P, and Williams J A. (2011a) Coexpressed RIG-I Agonist Enhances Humoral Immune Response to Influenza DNA Vaccine. J Virol 85: 1370-1383

Luke J., Vincent J M, Du S X, Whalen B, Leen A, Hodgson C P, and Williams J A. (2011b) Improved antibiotic-free plasmid vector design by incorporation of transient expression enhancers. Gene Ther 18: 334-343

In one embodiment of the present disclosure, all sequences that were not essential for *Escherichia coli* plasmid replication or mammalian cell expression of the target gene were eliminated. Synthetic eukaryotic mRNA leader and terminators were utilized in the vector design to limit DNA sequence homology with the human genome to reduce the possibility of chromosomal integration. The vectors encode a consensus Kozak translation initiation sequence and ATG start codon.

Preferably, target gene expression is driven from an optimized chimeric promoter-intron (SV40-CMV-HTLV-1 R synthetic intron). The boundary between the CMV promoter and the SV40 enhancer has been optimized resulting in dramatically improved expression in mammalian cells (Luke et al. 2011b). This chimeric CMV promoter achieves significantly higher expression levels than traditional human cytomegalovirus (CMV) promoter based vectors (Luke et al. 2009, 2011b)."

The amount of the adjuvant composition of the present disclosure and the amount of antigen, as well as the antigen production technology depend on the administration method selected. Those of skill in the art will be able to determine the appropriate ratio for such administration methods. Preferably, the adjuvant composition is present in an amount of from about 1% to 30%, by volume, of the total volume of the vaccine composition, where values and ranges such as 1% to 25%, 1% to 20%, 1% to 15%, 15% to 30%, 10% to 20%, 10% to 25%, 10% to 20%, 15% to 25%, 20% to 30%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, and 30% are envisioned. In a most preferred embodiment, the adjuvant composition is present in an amount of about 5% to 20% by volume. In an alternate embodiment, the ratio of the adjuvant composition of the present disclosure to the amount of antigen in the vaccine composition is as disclosed above, and preferably 1:1 to 1:5.

The present disclosure also provides for a vaccine composition or immunogenic composition. The vaccine composition comprises, consists of, or consists essentially of the adjuvants of the present disclosure and an antigen. The antigen may be any antigen suitable for administration in a vaccine composition. In a preferred embodiment, the antigen is DNA. The DNA can be in the form of double covalently closed circular supercoiled (dsCCSC) DNA, double stranded linear DNA (dsL), or double stranded relaxed circlar (dsRC) DNA. The DNA can also be in the form of single stranded circular covalently closed (ssCC) DNA or single stranded linear (ssL) DNA. Preferably, the DNA is selected from replication competent DNA and/or non-replication competent DNA, that has been incorporated into a plasmid that is dsCCSC DNA.

The vaccine or immunogenic composition of the present disclosure preferably comprises the adjuvant formulation of the present disclosure and a DNA component. Most preferably, the DNA is selected from replication competent DNA, or non-replication competent DNA, that has been incorporated into a plasmid that is dsCCSC DNA The art surrounding DNA-based vaccines provides that Ca++ is required for effective delivery and immune sensitization of the DNA component of the vaccine, where cationic systems are prevalent in the art. The vaccine of the present disclosure is surprisingly effective without the use of Ca++ or cations treatment of the DNA or delivery vehicle thereby representing an advancement in the art. Cationized liposomes are also not required for the vaccine or immunogenic composition of the present disclosure. In a further embodiment, the vaccine of the present disclosure requires only a small amount of DNA. Preferably, the DNA is present in an amount of from about 100 μg to 0.025 μg per dose where ranges and values such as 0.025 μg to 250 μg, 0.025 to 50 μg, 0.025 μg to 0.25 μg, 0.05 μg to 1 μg, 0.05 μg to 0.25 μg, 1 to 3 μg, 0.25 to 25 μg, 0.5 μg, 1 μg, 5 μg, 10 μg, 12 μg, 15 μg, 17 μg, 20 μg, 22 μg, 25 μg, 27 μg, 30 μg, 35 μg, 55 μg, 60 μg, 80 μg, 90 μg, 110 μg, 150 μg, 200 μg, and 225 μg are envisioned. This is preferably at least 30% less, more preferably at least 50% less, still more preferably at least 90% less, more preferably at least 40% less, more preferably at least 75% less, more preferably at least 90% less than the amount of DNA used in commercially available DNA-based vaccines, where values such as 40% less, 45% less, 55% less, 60% less, 70% less, 95% less, and 98% less are envisioned. In a preferred embodiment, the amount of DNA is determined per dose of vaccine.

A single dose vaccine or immunogenic composition is also provided by the present disclosure. The single dose vaccine comprises the adjuvant formulation of the present disclosure and at least one DNA component. The DNA is preferably selected from replication competent DNA, or non-replication competent DNA, that has been incorporated into a plasmid that is dsCCSC DNA. The single dose vaccine composition is effective at inducing a protective immune response in an animal after a single dose. For purposes of the present disclosure, a single dose means that only 1 administration of the vaccine is provided to the animal. Preferably, the single dose vaccine of the present disclosure is formulation without Ca++ treated DNA or liposomes.

The adjuvant composition of the present disclosure is preferably shelf stable for at least 6 months, more preferably at least 12 months, still more preferably at least 18 months, and even more preferably at least 24 months or longer. The stability preferably includes ability to keep biophysical and efficacy features after incubation for long periods of time at either at room temperature (about 60° F. to 80° F.; 18° C. to 26° C.) or in refrigerated temperatures (2° C. to 7° C.). The adjuvant composition of the present disclosure can also be frozen (−18° C. to −22° C.; −40° C. to −85° C. or freeze dried and stored at refrigerated temperatures (2° C. to 7° C.) and when resuspended after being freeze dried.

The present disclosure additionally provides for a method of vaccinating animals or humans. The method preferably comprises the step of administering the vaccine or immunogenic composition of the present disclosure to a recipient thereof. Alternatively, the method of the present disclosure comprises the steps of combining the adjuvant of the present disclosure with an antigen to form a composition and administering the composition to an animal or human in need thereof. Preferably, the antigen is one typically utilized in an immunogenic composition or vaccine composition and is preferably capable of eliciting an immune response in the recipient. The recipient is preferably a human or animal. In an embodiment where the recipient is an animal, the animal is preferably selected from, but not limited to, the group consisting of birds, pigs, cows, horses, dogs, cats, sheep, mules, monkeys, companion animals, and other mammals.

The present disclosure also provides for a method of eliciting an immune response in an animal, where the steps of the method comprise vaccinating an animal at least a single time with the vaccine or immunogenic composition of the present disclosure. Subsequent doses of vaccine are also envisioned, where the vaccine composition may be administered two, three, four, or five times.

The antigen, for purposes of the vaccine or immunogenic composition of the present disclosure, can be any antigen or combination of antigens suitable to induce an immunogenic response in a recipient. The recipient may be an animal or a human. The antigen for use in this disclosure may be any desired antigen falling within the definition set forth above. Antigens are commercially available or one of skill in the art is capable of producing them. In a preferred embodiment, the antigen is a DNA preferably selected from replication competent DNA, or non-replication competent DNA, that has been incorporated into a plasmid that is dsCCSC DNA. The DNA vaccine can encode the sequence for any gene that is the target of an immune response in the recipient. Gene sequences that could be encoded in the DNA vaccine include genes or gene motifs that encode an immunogenic sequence that are selected from, but not limited to Porcine Reproductive and Respiratory Syndrome (PRRS); *Mycoplasma hyopneumoniae* (M hyo); *Porcine proliferative enteritis*; Bovine Viral Diarrhea Virus (BVD); Border's Disease, *Leptospirosis*; Brucellosis caused by bacteria of the genus *Brucella; Clostridium; Tetanus toxemia*, caused by a specific neurotoxin produced by *Clostridium tetani; Salmonella* spp; *Escherichia coli*; Swine Pox; *Eperythrozoonosis*; Classical Swine Fever (CSF) or African Swine Fever (ASF); *Pneumonic pasteurellosis* and Streptococci, caused by *Pasteurella multocida* and various species of streptococci, typically *S. suis; Streptococcal meningitis*; Pseudorabies; Swine Influenza Virus; Spirochaetal colitis, caused by the *Brachyspira pilosicoli* bacteria; Swine dysentery, caused by the bacteria *Brachyspira hyodysentheriae*; coronavirus; Porcine Parvovirus; *Actinobacillus pleuropneumonia*; Glässers Disease, caused by the bacterium *Haemophilus parasuis* (Hps); Exudative epidermitis, caused by the bacterium *Staphylococcus hyicus*; Swine erysipelas, caused by a bacterium, *Erysipelothrix rhusiopathiae; Eperythrozoonosis*

(Epe), caused by a bacterium called *Eperythrozoonosis suis; Encephalomyocarditis*; Herpes Virus; Porcine Cytomegalovirus Infection (PCMV), caused by a herpes virus; Japanese B Encephalitis Virus (JE); Porcine Epidemic Diarrhoea (PED), caused by a coronavirus; Porcine Respiratory Corona Virus Infection (PRCV); Rotavirus; Rabies; Swine Vesicular Disease (SVD); Tuberculosis, caused by *Mycobacterium tuberculosis*; virus of vesicular exanthema of swine (VES); Vesicular Stomatitis (VS) virus; and Eastern equine encephalomyelitis viruses (EEEV).

The antigenic moiety making up the vaccine or immunogenic composition can be either a modified-live or killed microorganism, or a natural product purified from a microorganism or other cell including, but not limited to, tumor cell, a synthetic product, a genetically engineered protein, peptide, polysaccharide or similar product, or an allergen. The antigenic moiety can also be a subunit of a protein, peptide, polysaccharide or similar product. The antigen may also be the genetic antigens, i.e., the DNA or RNA that engenders or induces an immune response. Representative of the antigens that can be used according to the present disclosure include, but are not limited to, natural, recombinant or synthetic products derived from viruses, bacteria, fungi, parasites and other infectious agents in addition to autoimmune diseases, hormones, or tumor antigens which might be used in prophylactic or therapeutic vaccines and allergens. The viral or bacterial products can be components which the organism produced by enzymatic cleavage or can be components of the organism that were produced by recombinant DNA techniques that are well known to those of ordinary skill in the art. Because of the nature of the disclosure and its mode of delivery it is very conceivable that the disclosure would also function as a delivery system for drugs, such as hormones, antibiotics and antivirals. Examples of antigens suitable for use in the vaccine composition of the present disclosure, include, but are not limited to Porcine Reproductive and Respiratory Syndrome (PRRS); *Mycoplasma hyopneumoniae* (M hyo); *Porcine proliferative enteritis*; Bovine Viral Diarrhea Virus (BVD); Border's Disease, *Leptospirosis*; Brucellosis caused by bacteria of the genus *Brucella; Clostridium; Tetanus toxemia*, caused by a specific neurotoxin produced by *Clostridium tetani; Salmonella* spp; *Escherichia coli*; Swine Pox; *Eperythrozoonosis*; Classical Swine Fever (CSF) or African Swine Fever (ASF); *Pneumonic pasteurellosis* and Streptococci, caused by *Pasteurella multocida* and various species of streptococci, typically *S. suis; Streptococcal meningitis*; Pseudorabies; Swine Influenza Virus; Spirochaetal colitis, caused by the *Brachyspira pilosicoli* bacteria; Swine dysentery, caused by the bacteria *Brachyspira hyodysentheriae*; coronavirus; Porcine Parvovirus; *Actinobacillus pleuropneumonia*; Glässers Disease, caused by the bacterium *Haemophilus parasuis* (Hps); Exudative epidermitis, caused by the bacterium *Staphylococcus hyicus*; Swine erysipelas, caused by a bacterium, *Erysipelothrix rhusiopathiae; Eperythrozoonosis* (Epe), caused by a bacterium called *Eperythrozoonosis suis; Encephalomyocarditis*; Herpes Virus; Porcine Cytomegalovirus Infection (PCMV), caused by a herpes virus; Japanese B Encephalitis Virus (JE); Porcine Epidemic Diarrhoea (PED), caused by a coronavirus; Porcine Respiratory Corona Virus Infection (PRCV); Rotavirus; Rabies; Swine Vesicular Disease (SVD); Tuberculosis, caused by *Mycobacterium tuberculosis*; virus of vesicular exanthema of swine (VES); Vesicular Stomatitis (VS) virus; and Eastern equine encephalomyelitis viruses (EEEV). Alternatively, the vaccine of the present disclosure can encode the sequence for a gene sequence selected from, but not limited to, those present in Adeno-associated virus, Aichi virus, Australian bat lyssavirus, BK polyomavirus, Banna virus, Barmah forest virus, Bunyamwera virus, Bunyavirus La Crosse, Bunyaivrus snowshoe hare, Cercopithecine herpes virus, Chandipura virus, Chikungunya virus, Cossavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68,70, Human herpesvirus 1, Human herpesvirus 2, Human herpesvirus 6, Human herpesvirus 7, Human herpesvirus 8, Human Immunodeficiency virus, Human papillomavirus 1, Human papillomavirus 2, Human papillomavirus 16, 18, Human parainfluenza, Human parovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomenigitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Polio virus, Punta toro phlebovirus, Puumala virus, Rabies virus, Rift valley fever virus, Rosavirus A, Ross River virus, Rotavirus A, Rotavirus B, Rotavirus C, Rubella virus, Sagiyama virus, Salivirus A, Sandfly fever sicillian virus, Sapporo virus, Semliki forest virus, Seoul virus, Simiam foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, Zika virus, and combinations thereof. As understood by those of skill in the art and the usefulness of the vaccine with any type of antigen, all variations of the antigen including whole organisms, macromolecules, subunits, nucleic acids, expressed proteins, and combinations thereof are contemplated by the present disclosure.

The method of vaccinating of the present disclosure preferably includes administration of the composition comprising the adjuvant of the present disclosure and an antigen, where administration is needleless or injected. For purposes of embodiments of the present disclosure incorporating a DNA component, the administration method is preferably intramuscularly, subcutaneously or transdermal administration, although other administration methods may be employed. In one embodiment, the administration method is selected from the group consisting of topical, intramuscular, nasal, oral, transdermal, mucosal, needless administration methods and subcutaneous. Needleless administration methods include, but are not limited to, vaccine guns, transdermal patches, aerosols, mucosal administration methods, skin adhesion methods, dry particle projectiles, wet projectiles, gold/inert particle guns, and pneumatic guns.

Further, the present disclosure provides for a method of administering a vaccine composition to a pig. The method preferably includes the step of combining the adjuvant composition of the present disclosure with an antigen and administering the vaccine composition to a pig in need thereof. The adjuvant composition of the present disclosure is particularly suited to transdermal delivery because it allows antigens which normally have difficulty being absorbed transdermally to be absorbed through the skin of the recipient. The adjuvant of the present disclosure preferably provides for 0.001% to 80% higher absorption of antigens via the skin, when compared to other adjuvant compositions. Preferably in such embodiments, the adjuvant contains Labrafac™ as the lipophile.

It should be understood that every maximum numerical limitation provided in the specification includes every lower numerical limitation as if it were expressly written herein. Every minimum numerical limitation provided in the specification includes every higher limitation as if it were expressly written herein. Every numerical range provided herein expressly includes every narrower numerical range that falls within the broader numerical range, as if such narrower numerical range was expressly written herein.

The composition and methods disclosed in the present application can comprise, consist essentially of, or consist of the essential elements and limitations of the disclosure described herein, as well as any optional or additional ingredients, components, steps, or limitations described herein or otherwise useful in compositions and methods such as those described herein.

EXAMPLES

Example 1

This example illustrates the method of production for an adjuvant exemplary of those provided by the present disclosure.

Materials and Methods

The Materials used were as follows:

A. Labrafac™ Lipophile WL1349 (Gattefossé Catalog No. 3139)

B. Carbopol® 974P NF Polymer(Lubrizol Catalog No. CBP974PNF)

C. Dulbecco's Phosphate Buffered Saline without Calcium or Magnesium (Cellgro Catalog No. 21-031-CV) or equivalent D. Cholesterol, Plant-Derived, (Avanti Catalog No. 700100P)

E. Ethanol, 100% Solution, (Acros Catalog No. 61509-0010) or equivalent

F. Quil-A, (Brenntag Catalog Purified Saponin Quil-A, Lyophilized)

G. 5N Sodium hydroxide, (VWR Catalog No. BDH3225-1) or equivalent

TABLE 1

Formulation of Adjuvant 06 Stock

| Ingredient | Amount Required to Prepare 10,000 mL |
|---|---|
| Gattefossé-Labrafac ™ Lipophile WL1349 | 49.5 mL |
| Carbopol ® 974P NF Polymer | 25.0 g |

TABLE 1-continued

Formulation of Adjuvant 06 Stock

| Ingredient | Amount Required to Prepare 10,000 mL |
|---|---|
| Dulbecco's Phosphate Buffered Saline without Calcium or Magnesium | Q.S. 10,000 mL |

TABLE 2

Cholesterol Stock

| Ingredient | Amount Required |
|---|---|
| Cholesterol, Plant-Derived | 0.45 g |
| Ethanol, 100% Solution | 100 mL |

A cholesterol stock was then prepared by adding the cholesterol to ethanol. It was then mixed until dissolved. The solution was then sterile-filtered using a 0.2 μm filter. The solution was then stored at 2-7° C.

TABLE 3

Quil-A Stock

| Ingredient | Amount Required |
|---|---|
| Quil-A Saponin | 0.31 g |
| Reverse-Osmosis/Deionized (RO/DI) Water | 25 mL |

Next, a Quil-A stock was prepared by adding Quil-A Saponin to RO/DI water where it was mixed until dissolved. The solution was then sterile-filtered using a 0.2 μm filter. Next, the solution was stored at 2-7° C. The stock was a 1% as a 5× stock for Quil-A.

Preparation of Adjuvant 06

A 1:5 dilution of the Quil A stock was prepared, using the adjuvant 06 stock, by adding 20 mL of Quil A to 80 mL of adjuvant 06 stock and it was mixed by swirling. Next, 56 mL of Cholesterol stock was added to the bulk adjuvant 06 stock. Then 100 mL of the 1:5 dilution of the Quil A was added to the remaining bulk adjuvant 06 stock that now contained 56 mL of the cholesterol stock. The adjuvant mixture was then mixed for approximately 15 minutes. While it was being mixed, the adjuvant was aseptically aliquoted into sterile 60 mL PETG bottles at 50 mL aliquots. Each bottle was then sealed with a screw top cap. The bottles of Adjuvant 06 were then stored for not more than two years at 2-7° C.

Preparation of Adjuvant 05

Made as described above in Example 1 only no Quil A or Cholesterol is used in this formulation.

Preparation of Adjuvant 01

Made as described above for Example 1 only Lecithin is substituted for Labrafac™

Preparation of Adjuvant 03

Made as above for Example 1 only Lecithin is substituted for Labrofec, and no Quil A or Cholesterol is added.

Preparation of Adjuvant 02

Made as above for Example 1 only Lecithin is substituted for Labrafac™, and the Cholesterol is 1:10 of the concentration described in Example 1, Quil A concentration remains the same as described in Example 1.

Instructions for Use

The amount of stock of Adjuvant 06 described above can be calculated to mix with antigen using 1 part 5× stock Adjuvant 06 with 4 parts antigen to make a 1× stock for these studies. The 5× stock can also be diluted to form concentrations of antigen at 2× (1 part 5× Adjuvant 06 with 2.5 parts antigen), or 4× (1 part 5× Adjuvant 06 with 0.25 parts antigen).

The container of Adjuvant 06 should be mixed thoroughly before use. A small amount of Adjuvant 06 was aseptically drawn up with a sterile syringe and 18 gauge needle, and then evacuated to remove all air from the syringe. The desired amount of Adjuvant 06 was then steadily pulled up into the syringe. The measured volume of Adjuvant 06 stock was then added to the antigen and mixed thoroughly.

Example 2

The purpose of this study was to determine whether two different adjuvant formulations, each separate embodiments of the present disclosure, could be tested in mice when diluted to the concentration intended for use with vaccines.

Materials and Methods

Two killed K99 *E. coli* vaccines, one adjuvanted and one prepared in PBS, were also included in the study to determine whether the addition of an antigen would have a different effect on the mice compared to the same adjuvant formulation tested alone.

Adult female CF-1 mice approximately 6 weeks in age with an average weight of 27 g were inoculated with 0.5 ml of each of the five different adjuvant formulations diluted to a final 1× concentration. Mice were also inoculated with 0.5 ml of each killed K99 *E. coli* vaccine. Each treatment group consisted of eight mice inoculated either by subcutaneous injection in the back of the neck or by intraperitoneal injection. All mice were housed for seven days post-inoculation and observed for health.

All mice inoculated via subcutaneous injection in the back of the neck appeared to be healthy seven days post-inoculation, however three of the eight mice given the adjuvanted killed K99 *E. coli* vaccine exhibited lesions at the injection site by day 7 of the study. At least six of the eight mice in each group inoculated via intraperitoneal injection died between 24 and 48 hours post-inoculation.

Animals

Sixty-four female CF-1 mice sourced from Charles River Laboratories were approximately 6 weeks (44 days) old at the time of test article administration. Upon receipt the mice weighed an average of 19 grams. The mice were weighed again prior to test article administration on day 0 and weighed an average of 27 grams.

Test Articles

Adjuvants

Adjuvant 06 (Example 1)—5×

Adjuvant 06 (Example 1)—5×

Dulbecco's Phosphate Buffered Saline (DPBS); Cellgro, catalog: 21-031-CV Lot: 21031439 Exp. 30Sep16

Killed K99 *E. coli* Vaccines

Vaccine containing Adjuvant 06 4× Example 1, Killed *E. coli* expressing K99 pili Vaccine containing PBS, Killed *E. coli* expressing K99 pili Methods Study Time Line

TABLE 4

Study Time Line

| Date | Day of Study | Description |
|---|---|---|
| 3 Feb. 2014 | −44 | Birth date |
| 12 Mar. 2014 | −7 | Receipt of mice at animal facility |
| 19 Mar. 2014 | 0 | Treatment administration to all groups |
| 26 Mar. 2014 | 7 | End of study |

Study Design

TABLE 5

Study Design

| Treatment Group | Treatment Description[2] | Number of Animals | Route of Inoculation[1] | Days Observed for Health |
|---|---|---|---|---|
| T01 | Adjuvant 05 4× | 8 | SC | 0-7 |
| T02 | Adjuvant 06 4× | 8 | SC | 0-7 |
| T03 | Killed K99 + Adjuvant 01 4× | 8 | SC | 0-7 |
| T04 | Killed K99 + PBS | 8 | SC | 0-7 |
| T05 | Adjuvant 05 4× | 8 | IP | 0-7 |
| T06 | Adjuvant 06 4× | 8 | IP | 0-1 |
| T07 | Killed K99 + Adjuvant 01 4× | 8 | IP | 0-1 |
| T08 | Killed K99 + PBS | 8 | IP | 0-7 |

[1]SC—Subcutaneous injection in back of neck; IP = Intraperitoneal injection
[2]Concentration of 4× as calculated from Example 1.

Animal Receipt, Acclimation and Randomization

Upon receipt mice were weighed, five at a time, and each mouse was placed into a separate cage. This process was repeated until there were four mice placed per cage.

Daily health observations were performed during the seven day acclimation period.

Cages 1-16 were randomly assigned to treatment groups T01-T08 by drawing two cage numbers from a container and assigning them to group T01. The next two cage numbers drawn were assigned to group T02 and so on until all cages were assigned to a treatment group. See Table 4 for the cage numbers assigned to each treatment group.

Test Article Preparation

All test article preparation was performed aseptically on the day of administration.

Adjuvant Preparation

The bottle of the 5× adjuvant stock as described in Example 1 was allowed to warm to room temperature and then inverted a minimum of 30 times to mix. To make 4× adjuvant the appropriate adjuvant was diluted 1:1.25 with DPBS (0.25 parts DPBS+1 part adjuvant) and mixed by inverting a minimum of 30 times. The prepared test article was aliquoted into two separated sterile 5 ml transport tubes and labeled for the appropriate treatment groups.

Killed K99 Vaccines

The Killed K99+PBS vaccine which was stored at 2-7° C. prior to use in this study. The vaccine bottles were allowed to warm to room temperature and then inverted to mix before the material was removed directly from the vaccine vial to inoculate the appropriate treatment groups.

Treatment Administration

Mice were examined for health before administration of the test articles. Two cages of mice, eight mice total, were administered 0.5 ml of each test article. The subcutaneous (SC) injection was administered in the back of the neck using either a 25 g, ⅝" or a 25 g, 1" needle with 3 ml syringe. The intraperitoneal (IP) injection was administered using a 25 g, ⅝" needle with a 3 ml syringe. All treatment administration and time was recorded.

Weights

The mice were weighed using a bench top balance upon receipt in groups of 5 and the average weight of that group was determined.

Just prior to Day 0 (test article administration) the weight per mouse was determined using the same balance as upon receipt. Each cage was weighed. The value recorded for that cage was divided by the number of mice in that cage (4). The reported value was the cage average.

Health Observations

Health observations of the mice were performed at least once per day through day 7 of the study. All health observations were recorded.

Mice were observed for health approximately 82-89 minutes after the last test article was administered for the day 0 observations.

Measurable Criteria

The primary variable or outcome was the presence/absence of adverse events during the 7 day study attributable to the test article. This variable was determined for each adjuvant and route of administration. There were two observations recorded:

Site injection adverse events: lesions observed during the 7 day in-life stage at the site of injection were recorded.

Mortality: mortality was recorded if a mouse was found dead or was culled due to morbidity.

Results and Conclusions

The average weight of all the mice at the time of test article administration was 26.87 g.

Health Observations

None of the mice inoculated via SC injection with any of the adjuvants or the killed K99+PBS vaccine demonstrated an adverse reaction through the 7-day study period. At least six of the eight mice in each group inoculated via IP injection with any of the adjuvants died within 24 to 48 hours post-inoculation. Only the mice inoculated via IP injection with the killed K99+PBS vaccine remained healthy during the 7-day study period. Table 5 shows the mice that died during the study.

TABLE 6

Summary of Mouse Deaths During the Study

| Treatment Group | Description | Average Weight of Mice (g) | Inoculation Route | # Healthy Mice/Total Inoculated: 24 hours Post-Inoculation | # Healthy Mice/Total Inoculated: 7 Days Post-Inoculation |
|---|---|---|---|---|---|
| T01 | Adjuvant 05 4× | 26.57 | SC | 8/8 | 8/8 |
| T02 | Adjuvant 06 4× | 26.55 | SC | 8/8 | 8/8 |
| T03 | Killed K99 + Adjuvant 01 4× | 26.96 | SC | 8/8 | 8/8* |
| T04 | Killed K99 + PBS | 28.14 | SC | 8/8 | 8/8 |
| T05 | Adjuvant 05 4× | 27.25 | IP | 1/8 | 1/8 |
| T06 | Adjuvant 06 4× | 26.21 | IP | 0/8 | 0/8 |
| T07 | Killed K99 + Adjuvant 01 4× | 26.84 | IP | 0/8 | 0/8 |
| T08 | Killed K99 + PBS | 28.57 | IP | 8/8 | 8/8 |

*Mice were healthy throughout study, but had developed lesions at the injection site by day 7.

Discussion

Based on the results of this study, it appears as though vaccines prepared with any of the five adjuvant formulations tested at 4× concentration described in Example 1 in this study may be able to undergo satisfactory mouse safety testing via 9CFR 113.33 if the final product was administered via SC injection in the back of the neck.

Development of an injection site lesion may be possible when the adjuvant combined with an antigen is administered via this route, however, the lesion is unlikely to result in an unsatisfactory safety test as no other adverse reactions were observed.

Care was taken to ensure that the mice were above the pre-determined weight of 22 g, but no older than 7 weeks in age.

Conclusions

Adjuvanted vaccines prepared with Adjuvant formulations 06, 05 or 01 at 4× concentration described in Example 1 can be used and are capable of satisfactory mouse safety results when tested per 9CFR 113.33 if administered via subcutaneous injection in the back of the neck.

Example 3

This example illustrates the efficacy of the claimed adjuvant compositions with an avian flu H5 DNA vaccine.

Materials and Methods 160 male and female pathogen-free chickens were utilized for this study. The Study Design was as follows in Table 6 below. Each treatment group except T01 was vaccinated with H5 Plasmid DNA Lot Number DNA130414TKWI. This is a backbone DNA derived from pCIneo (Promega) containing a eukaryotic promoter (CMV early) and PolyA-addition termination site (SVV40) flanking a multiple cloning site (MCS). The plasmid has a selection marker neomycin for selection in eukaryotic cells and an ampicillin resistance marker for selection in *E. coli* during amplification of the plasmid in fermentation. The hemagglutination gene (HA) from the H5N9 turkey/WI/68 isolate of avian influenza is cloned into the MCS of the vector. This DNA was isolated and designated at as AIV H5 DNA. A second DNA was prepared containing a different DNA backbone this DNA had the same H5N9 turkey/WI/68 AIV HA gene insert, but was constructed the Nature Technology (NT) for these studies. The NT plasmid backbone contains NTC8685-eRNA41H-U79456 HA and is designated AIV H5 DNA (nt).

TABLE 7

| Treatment Group Descriptions | | | | | | Blood |
|---|---|---|---|---|---|---|
| Trt Group[1] | Description[4] | Route[2] | No. of Chickens | Dose (ml)[3] | Day | Collections Day |
| T01 | Negative Control (Uninoculated) | N/A | 10 | N/A | 0, 14 | 14, 28 |
| T02 | AIV H5 DNA (bbl) + 4× Adjuvant 01 | IM | 10 | 0.4 | 0, 14 | |
| T03 | AIV H5 DNA (bbl) + 2× Adjuvant 01 | IM | 10 | 0.4 | 0, 14 | |
| T04 | AIV H5 DNA (bbl) + 1× Adjuvant 01 | IM | 10 | 0.4 | 0, 14 | |
| T05 | AIV H5 DNA (bbl) + 4× Adjuvant 02 | IM | 10 | 0.4 | 0, 14 | |
| T06 | AIV H5 DNA (bbl) + 2× Adjuvant 02 | IM | 10 | 0.4 | 0, 14 | |
| T07 | AIV H5 DNA (bbl) + 1× Adjuvant 02 | IM | 10 | 0.4 | 0, 14 | |
| T08 | AIV H5 DNA (bbl) + 4× Adjuvant 03 | IM | 10 | 0.4 | 0, 14 | |
| T09 | AIV H5 DNA (bbl) + 2× Adjuvant 03 | IM | 10 | 0.4 | 0, 14 | |
| T10 | AIV H5 DNA (bbl) + 1× Adjuvant 03 | IM | 10 | 0.4 | 0, 14 | |
| T11 | AIV H5 DNA (bbl) + 4× Adjuvant 05 | IM | 10 | 0.4 | 0, 14 | |
| T12 | AIV H5 DNA (bbl) + 2× Adjuvant 05 | IM | 10 | 0.4 | 0, 14 | |
| T13 | AIV H5 DNA (bbl) + 1× Adjuvant 05 | IM | 10 | 0.4 | 0, 14 | |
| T14 | AIV H5 DNA (bbl) + 4× Adjuvant 06 | IM | 10 | 0.4 | 0, 14 | |
| T15 | AIV H5 DNA (bbl) + 2× Adjuvant 06 | IM | 10 | 0.4 | 0, 14 | |
| T16 | AIV H5 DNA (bbl) + 1× Adjuvant 06 | IM | 10 | 0.4 | 0, 14 | |

[1]For this study, the treatment group (TG) designation identifies the chickens and the test article.
[2]IM—Intramuscular injection.
[3]Each chicken will be inoculated with 0.2 ml volume in the left breast muscle and 0.2 ml volume in the right breast muscle.
[4]AIV H5 DNA (bbl) included in each treatment except control T01.

TABLE 8

| Study Timeline | |
|---|---|
| Day | Activity |
| Prior to Day 0 | Daily Clinical Observations/Acclimation |
| Day 0 | Test Article Administration |
| Day 14 | Blood Collection |
| | Test Article Booster Administration |
| Day 28 | Blood Collection |
| Days 0-28 | Daily Clinical Observations |
| Day 28 | End of Study |

Study Methods

Randomization and Acclimation

Daily health observations for the chickens were recorded on all study birds during the acclimation phase. Birds will be acclimated for a minimum of three days. Clinical observations were performed daily and recorded.

Administration Route

All birds were administered the test articles by intramuscular injection into the left and right sides of the breast.

Test Article Administration—Days 0 and 14

On Day 0 birds were examined for normal health and appearance and enrolled in the study. One cage will represent one treatment group.

The ten birds in T01 were not inoculated to serve as the negative control. The ten birds in each of the remaining treatment groups (T05-T16) were inoculated with the appropriate test article by intramuscular injection on day 0 and day 14 of the study.

Sample Collection and Testing

Blood was collected from each bird on day 14 (prior to the day 14 booster administration of test articles) and day 28 according to site procedures. Blood was allowed to clot and then centrifuged to collect serum. The serum was then stored at −18±5° C. until tested if testing was not going to occur within 48 hours of collection and/or after serum has been tested. Serum was then assayed for the level of seroconversion via Hemagglutination Inhibition Assay (HAI).

Health Observations and Adverse Events

Following administration of the test articles, clinical observations were recorded at least once daily until the end of the study (day 28). All clinical observations were recorded.

Assessment of Results/Data Analysis

Serum samples were assayed for seroconversion via HAI. The HAI titer was then determined for each serum sample in each treatment group. The HAI titers of the birds inoculated with 1× adjuvant were then compared to the titers of the birds inoculated with 2× and 4× of each adjuvant formulation to demonstrate the concentration range of each adjuvant for efficacy using a DNA/adjuvant formulation.

Test Article Preparation

The Test articles were prepared on the day of administration and transported to the clinical site.

Preparation of the test articles was conducted in biosafety cabinets using aseptic techniques. Final formulations of all test articles were incubated at room temperature for 30±5 minutes prior to administration to birds.

Test Articles

AIV H5 Plasmid DNA (bbl) Lot Number DNA130414TKWI; Tested for purity and quality.

Dulbecco's Phosphate Buffered Saline (DPBS); Cellgro, catalog: 21-031-CV Lot: 21031439.

TABLE 9

| Adjuvant Stock Identification | |
|---|---|
| Adjuvant from Example 1[1] | Manufacturer |
| Adjuvant 01 | BBL |
| Adjuvant 02 | BBL |
| Adjuvant 03 | BBL |
| Adjuvant 05 | BBL |
| Adjuvant 06 | BBL |

[1]Formulations were described in Example 1 for each adjuvant.

TABLE 10

| Test Article Formulation for each Treatment Group | | |
|---|---|---|
| Trt Group | AIV H5 Plasmid DNA per 0.4 ml dose | Adjuvant from Example 1 |
| T02 | 30 ug | 4× Adjuvant 01 |
| T03 | 30 ug | 2× Adjuvant 01 |
| T04 | 30 ug | 1× Adjuvant 01 |

TABLE 10-continued

| Test Article Formulation for each Treatment Group | | |
|---|---|---|
| Trt Group | AIV H5 Plasmid DNA per 0.4 ml dose | Adjuvant from Example 1 |
| T05 | 30 ug | 4× Adjuvant 02 |
| T06 | 30 ug | 2× Adjuvant 02 |
| T07 | 30 ug | 1× Adjuvant 02 |
| T08 | 30 ug | 4× Adjuvant 03 |
| T09 | 30 ug | 2× Adjuvant 03 |
| T10 | 30 ug | 1× Adjuvant 03 |
| T11 | 30 ug | 4× Adjuvant 05 |
| T12 | 30 ug | 2× Adjuvant 05 |
| T13 | 30 ug | 1× Adjuvant 05 |
| T14 | 30 ug | 4× Adjuvant 06 |
| T15 | 30 ug | 2× Adjuvant 06 |
| T16 | 30 ug | 1× Adjuvant 06 |

CaCl precipitation: final concentration of:
Plasmid DNA: 75 ug/mL
Calcium Chloride: 2.68 mM
Sodium Phosphate: 2.68 mM
Sodium Citrate: 0.669 mM
Results and Conclusions

TABLE 11

| Seroconversion data and GMT at Day 13 and 28 of the study | | | | | |
|---|---|---|---|---|---|
| | | Day 13 (post first vacc) | | Day 28 (14 d post boost) | |
| NBHO2502 Group | # Birds | Day 13 # sero+ | Day 13 GMT | Day 28 # sero+ | Day 28 GMT |
| Negative Control (Uninoculated) | 10 | 0 | 2.0 | 0 | 2.0 |
| AIV H5 DNA (bbl) + 4× Adjuvant 01 | 10 | 1 | 2.3 | 7 | 42.2 |
| AIV H5 DNA (bbl) + 2× Adjuvant 01 | 9 | 3 | 3.4 | 8 | 37.3 |
| AIV H5 DNA (bbl) + 1× Adjuvant 01 | 10 | 1 | 2.5 | 10 | 64.0 |
| AIV H5 DNA (bbl) + 4× Adjuvant 02 | 10 | 2 | 2.6 | 10 | 64.0 |
| AIV H5 DNA (bbl) + 2× Adjuvant 02 | 10 | 5 | 4.9 | 9 | 55.7 |
| AIV H5 DNA (bbl) + 1× Adjuvant 02 | 10 | 3 | 3.5 | 10 | 78.8 |
| AIV H5 DNA (bbl) + 4× Adjuvant 03 | 10 | 4 | 3.7 | 9 | 59.7 |
| AIV H5 DNA (bbl) + 2× Adjuvant 03 | 10 | 6 | 6.1 | 10 | 119.4 |
| AIV H5 DNA (bbl) + 1× Adjuvant 03 | 10 | 1 | 2.3 | 9 | 26.0 |
| AIV H5 DNA (bbl) + 4× Adjuvant 05 | 10 | 3 | 3.2 | 10 | 157.6 |
| AIV H5 DNA (bbl) + 2× Adjuvant 05 | 10 | 0 | 2.0 | 10 | 111.4 |
| AIV H5 DNA (bbl) + 1× Adjuvant 05 | 10 | 2 | 3.0 | 10 | 84.4 |
| AIV H5 DNA (bbl) + 4× Adjuvant 06 | 10 | 3 | 3.0 | 10 | 119.4 |
| AIV H5 DNA (bbl) + 2× Adjuvant 06 | 10 | 1 | 2.3 | 9 | 39.4 |
| AIV H5 DNA (bbl) + 1× Adjuvant 06 | 10 | 1 | 2.3 | 8 | 24.3 |

Table 11 shows the summary of this study including the number of birds seroconverted and the GMT antibody titer for each treatment group after inoculation. The results indicated that low doses of DNA (30 ug or less per dose) can be used to vaccinate chickens by the IM route using Ca++ precipitated DNA. The Adjuvant 05 formulation at the 4× concentration as described by Example 1 was most efficacious indicating that these adjuvant formulations can be optimized and have a wide range of efficacy opportunity. Furthermore all birds at optimal doses were primed with as little as single dose of vaccine since all birds seroconverted after the second dose all the birds must have been primed after the first dose.

Example 4

This study illustrates the stability of the adjuvants of the present disclosure over 6 months.

Materials and Methods

Preparation of Stability Test Articles

Two different adjuvant formulations were combined with BSA for a target concentration of 50 ug BSA (bovine serum albumin)/dose. All test articles prepared were aseptically aliquoted into sterile glass vials with rubber stoppers and crimped shut.

Test article PBO/cold was prepared by aliquoting commercial phosphate buffered saline (PBS) into vials as described and stored at refrigerated temperature. Test articles BSA/PBS/RT and BSA/PBS/cold were prepared by adding 4 parts BSA and 1 part PBS for a target concentration of 500 ug/ml (50 ug/0.1 mL dose) and stored at ambient or refrigerated temperatures. Test articles BSA/Adj01/RT and BSA/Adj01/cold were prepared by adding 0.25 parts BSA and 1 part Adjuvant 01 (per Example 1) for a target concentration of 500 ug/ml (50 ug/0.1 mL dose) and stored at ambient or refrigerated temperatures. Test articles BSA/Adj06/RT and BSA/Adj06/cold were prepared by adding 0.25 parts BSA and 1 part Adjuvant 06 (per Example 1) for a target concentration of 500 ug/ml (50 ug/0.1 mL dose) and stored at ambient or refrigerated temperatures.

Study Methods

Acclimation

Daily health observations were recorded on all study animals during the acclimation phase. Animals were be acclimated for a minimum of six days.

Placement on Test Procedures

Mice were ear notched for identity. Mice were placed in study cages placing five mice per cage. The mice we also weighed during the 6 month testing.

Treatment Administration

Mice were examined for normal health and appearance and enrolled in the study. Mice were maintained according to treatment group with two cages containing five mice each representing a treatment group. The exception was for the mice receiving the placebo (PBO) which consisted of one cage containing five mice.

At the Day 0 time point, regardless of the "storage conditions", one vial of each treatment group was aseptically divided into three aliquots. One aliquot was administered to the mice immediately (Day 0). The second aliquot was stored at 2-7° C. until administered to the mice on Day 14 and was not considered as a "stability" sample. The third aliquot was maintained at 2-7° C. as a retention sample and also not considered a "stability" sample. All test articles were administered to mice subcutaneously dorsal between the shoulders.

Health Observations and Adverse Events

Clinical observations including adverse events were recorded daily until study completion.

Administration Route

All mice will be administered the test article via subcutaneous injection, dorsal between the shoulders.

Prescreen Sample Collection—Day −4 −0 (Baseline mice only)

Blood was collected and pooled from the baseline mice (the mice not used in the study) once between days—4 and 0 to obtain prescreen serum. No more than 10% of the total blood volume based on the average weight of the mice was collected at this time. Blood was allowed to clot and then centrifuged to collect serum. The serum was be pooled and stored at 2-7° C. or −18±5° C. until tested via ELISA to ensure the mice to be used in the study were seronegative to BSA.

TABLE 12

Treatment Group Descriptions

| Treatment Group Descriptions[1] | | | | | | Blood |
|---|---|---|---|---|---|---|
| Trt Group | Description | Route 1 | No. of Mice | Dose (mL) | Day | Collections Day |
| T01 | Placebo (PBS only) | SC | 5 | 0.1 | 0, 14 | 13 32 |
| T02 | 50 ug BSA + PBS | SC | 10 | 0.1 | 0, 14 | |
| T04 | 50 ug BSA + Adjuvant 06 4× | SC | 10 | 0.1 | 0, 14 | |
| T06 | 50 ug BSA + 05 Adjuvant 05 4× | SC | 10 | 0.1 | 0, 14 | |

[1]Adjvuants prepared as described in Example 1

TABLE 13

Summary of Stability Test Articles

| Test Article ID[1] | True Name[2] | Manufacturer | Storage Temp | Volume/ Vial (mL) | Number of Vials Prepared | Stability Testing Dates (month) | 6 Month Trt Group |
|---|---|---|---|---|---|---|---|
| PBO/cold | S-Placebo (PBS only) | Cellgro (Cat 21-031-CV) | 2-7° C. | 5 | 25 | 0, 6, 12, 18, 24 | T01 |
| BSA/PBS/cold | S-50 ug BSA + PBS | BBL | 2-7° C. | 5 | 26 | 0, 6, 12, 18, 24 | T02 |
| BSA/PBS/RT | S-50 ug BSA + PBS | | 18-27° C. | 5 | 26 | 0, 6, 12, 18, 24 | T03 |
| BSA/Adj06/cold | S-50 ug BSA + Adjuvant 06 | | 2-7° C. | 5 | 26 | 0, 6, 12, 18, 24 | T06 |
| BSA/Adj06/RT | S-50 ug BSA + Adjuvant 06 | | 18-27° C. | 5 | 26 | 0, 6, 12, 18, 24 | T07 |

[1]Remaining volume from each aliquot used to inoculate on days 0 and 14 will be destroyed on day of use. The remaining retention aliquot will be retained.

TABLE 14

Stability Test Article Descriptions

| Tart Grp | True Name[1] | Descriptor[2] | Storage Temperature[3] |
|---|---|---|---|
| T01 | S-Placebo (PBS only) | S-PBS/cold | 2-7° C. |
| T02 | S-50 ug BSA + PBS | S-BSA/cold | 2-7° C. |
| T03 | S-50 ug BSA + PBS | S-BSA/RT | 18-27° C. |
| T06 | S-50 ug BSA + Adjuvant 06 4× | S-BSA + 06/cold | 2-7° C. |
| T07 | S-50 ug BSA + Adjuvant 06 4× | S-BSA + 06/RT | 18-27° C. |

[1]500 ug/ml BSA stock, 50 ug BSA/dose

[2]Descriptor for each treatment group

TABLE 15

Fresh Test Article Descriptions

| | | | Storage Temperature[3] | | |
|---|---|---|---|---|---|
| Trt Grp | True Name[1] | Descriptor[2] | BSA | PBS | Adjuvant |
| T08 | F-50 ug BSA + PBS | F-BSA | −80 ± 10° C. | 18-27° C. | |
| T11 | F-50 ug BSA + Adjuvant 06 4× | F-BSA + 06/cold | | | 2-7° C. |
| T12 | F-50 ug BSA + Adjuvant 06 4× | F-BSA + 06/RT | | | 18-27° C.[5] |

[1]500 ug/ml BSA stock, 50 ug BSA/dose

[2]Descriptor for each treatment group

[3]Storage temperature of components used to prepare fresh test articles

[5]5× Adjuvant stocks stored in the same storage location and temperature as the stability samples stored at 18-27° C.

TABLE 16

| Clinical Study Design | | | | | | |
|---|---|---|---|---|---|---|
| Trt Grp[1] | Descriptor | Route[2] | No. Mice | Dose (mL) | Inocu-lation (Day) | Blood Collection (Day) |
| T01 | S-PBS/cold | SC | 5 | 0.1 | 0, 14 | 13, 28 |
| T02 | S-BSA/cold | SC | 10 | 0.1 | 0, 14 | |
| T03 | S-BSA/RT | SC | 10 | 0.1 | 0, 14 | |
| T06 | S-BSA + 06/cold | SC | 10 | 0.1 | 0, 14 | |
| T07 | S-BSA + 06/RT | SC | 10 | 0.1 | 0, 14 | |
| T08 | F-BSA | SC | 10 | 0.1 | 0, 14 | |
| T11 | F-BSA + 06/cold | SC | 10 | 0.1 | 0, 14 | |
| 112 | F-BSA + 06/RT | SC | 10 | 0.1 | 0, 14 | |
| Additional[3] | Baseline | N/A | 20 | N/A | N/A | ** |

[1]For this study, the treatment group (TG) designation will identify the mice and the test article
[2]Mice will be inoculated via subcutaneous injection dorsal, between the shoulders
[3]Additional mice NOT inoculated with test article; used to obtain baseline blood samples

TABLE 17

| Study Design | |
|---|---|
| Day | Activity |
| Days −6 to −8 | Daily Clinical Observations |
| Day −4-0 | Blood collection (baseline mice only)<br>mice bled one time within this period to obtain prescreen samples for confirmation of mice seronegativity via ELISA |
| Day 0 | Treatment Administration |
| Day 1-28 | Blood collection (baseline mice only)<br>mice bled periodically during this time to obtain baseline blood samples<br>Daily Clinical Observations |
| Day 13 | Blood collection |
| Day 14 | Treatment Administration |
| Day 28 | Blood collection |

Treatment Administration—Day 0

Mice were examined for normal health and appearance and enrolled in the study. Each cage represented a treatment group.

One vial of each treatment group preparation was aseptically divided into three aliquots. One aliquot was administered to the mice immediately (Day 0). One aliquot was stored at 2-7° C. until administered to the mice on Day 14. The last aliquot was maintained at 2-7° C. as a retention sample. All treatment group preparations (for each TG) were administered to mice subcutaneously dorsal between the shoulders according to the Study Design.

Sample Collection—Day 1-28 (Baseline mice only)

Blood was collected and pooled from the baseline mice (the mice not used in the study) as needed between days 1 and 28. No more than 10% of the total blood volume based on the average weight of the mice were collected within a 3-4 week period. Blood was allowed to clot and then centrifuged to collect serum. The serum was then pooled and stored at 2-7° C. or −18±5° C. until used as a negative control in the ELISA.

Sample Collection and Testing

Blood was collected from each inoculated animal on days 13 and 28. No more than 10% of the total blood volume based on the average weight of the mice was collected within a 3-4 week period. Blood was allowed to clot and then centrifuged to collect serum. The serum was then stored at 2-7° C. or −18±5° C. until tested. Serum was then assayed for the level of seroconversion via ELISA.

Treatment Administration—Day 14

All treatment group preparations (for each TG) were administered to mice via subcutaneous injection, dorsal between the shoulders according to the Study Design.

Health Observations and Adverse Events

Clinical observations were recorded daily following test article administration, as indicated in the study timeline.

Assessment of Analysis/Data Analysis

Serum samples were assayed for seroconversion via ELISA. The level of antibody production in each serum sample for each treatment group was determined. Antibody production in the mice administered Adjuvant+BSA was compared to the antibody production in mice administered the BSA positive control. Antibody production in mice administered the various adjuvant formulations was compared. Antibody production in the mice administered test articles that had been stored for stability analysis was compared to the mice administered test articles prepared fresh on day 0 of this study.

Antibody production levels in mice inoculated in this study was compared to the antibody levels produced in the first stability study conducted.

Descriptive statistics will be used when appropriate to determine effectiveness of all treatment groups compared to the negative control. Geometric means and statistical significance will be determined by performing two-tailed Student's t-test or other appropriate method.

Results and Conclusions

TABLE 18

| Mouse Stability GMT Values derived from ELISA Results BSA Adjuvant 06 on Stability | | | | | | | |
|---|---|---|---|---|---|---|---|
| | | Time 0 | | | 6 Month | | |
| | | Day 32 | | | Day 28/29 | | |
| Treatment Group | Descriptor | Geometric Mean[1] | Incidence | Normalized* | Geometric Mean[1] | Incidence | Normalized* |
| T01 | S-PBS/2-7° C. | 10 | 0/4 | | 20 | 0/5 | |
| T02 | S-BSA/2-7° C. | 290 | 8/10 | 1 | 149 | 8/10 | 1 |
| T03 | S-BSA/RT | | | | 243 | 8/10 | 1 |
| T06 | S-BSA + 06/2-7° C. | 27,160 | 10/10 | 93.7 | 28,522 | 10/10 | 191.4 |
| T07 | S-BSA + 06/RT | | | | 30,177 | 10/10 | 124.2 |
| T08 | F-BSA | | | | 98 | 6/10 | |
| T11 | F-BSA + 06/2-7° C. | | | | 17,743 | 10/10 | 119.1 |
| T12 | F-BSA + 06/RT | | | | 34,297 | 10/10 | 141.1 |

TABLE 19

| Data from blood collected | | | |
|---|---|---|---|
| Descriptor | Incidence[1] | Geometric Mean[2] | Normalization[3] |
| PBO | 0/5 | 10 | ND[4] |
| BSA/PBS | 8/10 | 290 | 93.7 |
| BSA/Adj06 | 10/10 | 27,160 | |

[1]# Mice Seroconverted/# Mice Treated
[2]A value of 10 used for no seroconversion
[3]Geomean BSA/Adj06 ÷ Geomean BSA/PBS
[4]Not done

TABLE 20

| Data at Time Point = 6 Months | | | |
|---|---|---|---|
| Descriptor | Incidence[1] | Geometric Mean[2] | Normalization[3] |
| S-PBO | 0/5 | 10 | Not determined |
| S-BSA/PBS/cold | 8/10 | 149 | 191.4 |
| S-BSA/Adj06/cold | 10/10 | 28,522 | |
| S-BSA/PBS/RT | 8/10 | 243 | 124.2 |
| S-BSA/Adj06/RT | 10/10 | 30,177 | |
| F-BSA/PBS | 6/10 | 98 | |
| F-BSA/Adj06/cold | 10/10 | 17,743 | 181.1 |
| F-BSA/Adj06/RT | 10/10 | 34,297 | 350.0 |

[1]# Mice Seroconverted/# Mice Treated
[2]A value of 10 used for no seroconversion
[3]Geomean BSA/Adj06 ÷ Geomean BSA/PBS

TABLE 21

| Geometric Means | | | | | |
|---|---|---|---|---|---|
| | Geometric Means | | | | |
| | | Time point - 6 Months | | | |
| Descriptor | Time point - 0 Month | Fresh | | Stability Cold - Storage (2-7° C.) | Stability Ambient - Storage (18-27° C.) |
| BSA/PBS | 290 | 98 | | 149 | 243 |
| | | Fresh-Cold | Fresh-Ambient | | |
| BSA/Adj06 | 27,160 | 17,743 | 34,297 | 28,522 | 30,177 |
| Normalized BSA/Adj06 | 97.3 | 181.1 | 350.0 | 191.4 | 124.2 |

The data shows that the adjuvants of the present disclosure were stable over a 6 month period when incubated with and without protein samples, which in this case was BSA. As can be seen from the data, all of the samples of adjuvant 06 were stable after 6 months. This data shows that the adjuvants of the present disclosure have shelf stability at ambient temperatures for at least 6 months. This allows for the ease of shipping, storage, and the use of the adjuvant either un-assembled or assembled with antigen.

Example 5

This example illustrates the efficacy of the DNA vaccine of the present disclosure administered subcutaneously without and Ca++ treatment of the DNA or adjuvant using different concentrations of the adjuvant formulations of the present disclosure by measuring their ability to elicit an immune response in specific pathogen free (SPF) chickens.

Materials and Methods

140 SPF chickens, both male and female, were used in the study. The Study Design is below in TABLE 22. Blood was collected on days 14 and 28 of the study.

TABLE 22

| Study Design Treatment Group Descriptions | | | | | |
|---|---|---|---|---|---|
| Trt Group[1] | Description | Route[2] | No. of Chickens | Dose (ml)[3] | Day |
| T01 | Placebo - PBS | SC | 10 | 0.4 | 0, 14 |
| T02 | AIV H5 DNA (bbl)[4] + 2× Adjuvant 03 | SC | 10 | 0.4 | 0, 14 |
| T03 | AIV H5 DNA (bbl)[4] + 2× Adjuvant 03 | IM | 10 | 0.4 | 0, 14 |
| T04 | AIV H5 DNA (nt)[5] + 2× Adjuvant 03 | IM | 10 | 0.4 | 0, 14 |
| T05 | AIV H5 DNA (nt)[5] + 4× Adjuvant 01 | SC | 10 | 0.4 | 0, 14 |
| T06 | AIV H5 DNA (nt)[5] + 2× Adjuvant 01 | SC | 10 | 0.4 | 0, 14 |
| T07 | AIV H5 DNA (nt)[5] + 4× Adjuvant 02 | SC | 10 | 0.4 | 0, 14 |
| T08 | AIV H5 DNA (nt)[5] + 2× Adjuvant 02 | SC | 10 | 0.4 | 0, 14 |
| T09 | AIV H5 DNA (nt)[5] + 4× Adjuvant 03 | SC | 10 | 0.4 | 0, 14 |
| T10 | AIV H5 DNA (nt)[5] + 2× Adjuvant 03 | SC | 10 | 0.4 | 0, 14 |
| T11 | AIV H5 DNA (nt)[5] + 4× Adjuvant 05 | SC | 10 | 0.4 | 0, 14 |

TABLE 22-continued

| Study Design<br>Treatment Group Descriptions | | | | | |
|---|---|---|---|---|---|
| Trt Group[1] | Description | Route[2] | No. of Chickens | Dose (ml)[3] | Day |
| T12 | AIV H5 DNA (nt)[5] + 2× Adjuvant 05 | SC | 10 | 0.4 | 0, 14 |
| T13 | AIV H5 DNA (nt)[5] + 4× Adjuvant 06 | SC | 10 | 0.4 | 0, 14 |
| T14 | AIV H5 DNA (nt)[5] + 2× Adjuvant 06 | SC | 10 | 0.4 | 0, 14 |

[1]For this study, the treatment group (TG) designation will identify the chickens and the test article.
[2]SC—Subcutaneous injection; IM—Intramuscular.
[3]Each chicken will be inoculated with a total of 0.4 mL
[4]BBL plasmid TKWI-001 (30 ug per dose)
[5]NT plasmid NTC8685-eRNA41H-U79456HA (30 ug per dose)
Note:
Treatment groups 02, 03 and 04 had DNA treated with Ca++, all treatment groups used 5× stock adjuvant as described in Example 1.

TABLE 23

| Study Timeline | |
|---|---|
| Day | Activity |
| Prior to Day 0 | Daily Clinical Observations/Acclimation |
| Day 0 | Test Article Administration |
| Day 14 | Blood Collection |
| | Test Article Booster Administration |
| Day 28 | Blood Collection |
| Days 0-28 | Daily Clinical Observations |
| Day 28 | End of Study |

Study Methods

Randomization and Acclimation

Birds were placed in study cages in the order they were removed from shipment boxes until all cages contained a total of ten birds. Birds were individually tagged for identification.

Daily health observations were recorded on all study birds during the acclimation phase. Birds were acclimated for a minimum of three days. Clinical observations were performed daily and recorded.

Administration Route

Birds were administered the test articles either by intramuscular injection into the left and right sides of the breast or by subcutaneous injection in a single site in the back of the neck.

Test Article Administration—Days 0 and 14

On Day 0 birds were examined for normal health and appearance and enrolled in the study. One cage represented one treatment group.

The ten birds in T01 were inoculated with PBS to serve as the negative control. The ten birds in treatment groups T03 and T04 were inoculated with the appropriate test article by intramuscular injection on day 0 and day 14 of the study. The remaining treatment groups T02, T05-T14, were inoculated with the appropriate test article by subcutaneous injection on day 0 and 14 of the study.

Health Observations and Adverse Events

Following administration of the test articles, clinical observations were recorded at least once daily until the end of the study (day 28).

Sample Collection and Testing

Blood was collected from each bird prior to the day 14 booster administration of test articles and day 28 according to site procedures. Blood collection was documented. Blood was allowed to clot and then centrifuged to collect serum. The serum was stored at 2-7 or −18±5° C. until tested and stored long term at −18±5° C. Serum was assayed for the level of seroconversion via Hemagglutination Inhibition Assay (HAI).

Assessment of Results/Data Analysis

Serum samples were assayed for seroconversion via HAI. The HAI titers were determined for each serum sample in each treatment group. The HAI titers of the birds inoculated with 4× adjuvant were compared to the titers of the birds inoculated with 2× of each adjuvant formulation to determine which concentration of each adjuvant is most effective.

The HAI titers in the birds administered the various adjuvant formulations were compared between each other.

Descriptive statistics were used when appropriate to determine effectiveness of all treatment groups compared to the negative control. Geometric means and statistical significance may be determined by performing two-tailed Student's t-test or other appropriate method.

Test Article Preparation

The Test articles were prepared on the day of administration and transported to the clinical site.

Preparation of the test articles were conducted in biosafety cabinets using aseptic techniques. The test articles were prepared according to pre-verified worksheets used to determine the volumes of each component. The pre-verified worksheets were maintained in the study file. Final formulations of all test articles were incubated at room temperature for 30±5 minutes prior to administration to birds.

Test Articles

BBL AIV H5 Plasmid DNA; Tested for purity and quality.

NT AIV H5 Plasmid DNA; Tested for purity and quality.

Dulbecco's Phosphate Buffered Saline (DPBS); Cellgro, catalog: 21-031-CV.

Results and Conclusions

TABLE 24

| Serology and GMT at Day 13 and Day 28 | | | | | | |
|---|---|---|---|---|---|---|
| | | | Day 13 | | Day 28 (14 d post boost) | |
| | Group | # Birds | D 13 sero+ | GMT | # sero+ | GMT |
| T01 | Placebo - PBS | 10 | 1 | 2.3 | 4 | 6.1 |
| T02 | AIV H5 DNA (bbl) + 2× Adjuvant 03 | 10 | 5 | 3.0 | 10 | 68.6 |
| T03 | AIV H5 DNA(bbl) + 2× Adjuvant 03 | 10 | 3 | 2.6 | 10 | 147.0 |
| T04 | AIV H5 DNA (nt) + 2× Adjuvant 03 | 10 | 0 | 2.0 | 0 | 2.0 |

TABLE 24-continued

Serology and GMT at Day 13 and Day 28

| | Group | # Birds | Day 13: D 13 sero+ | Day 13: GMT | Day 28 (14 d post boost): # sero+ | Day 28 (14 d post boost): GMT |
|---|---|---|---|---|---|---|
| T05 | AIV H5 DNA (nt) + 4× Adjuvant 01 | 10 | 1 | 2.3 | 7 | 17.1 |
| T06 | AIV H5 DNA (nt) + 2× Adjuvant 01 | 10 | 0 | 2.0 | 8 | 21.1 |
| T07 | AIV H5 DNA (nt) + 4× Adjuvant 02 | 10 | 2 | 2.6 | 8 | 17.1 |
| T08 | AIV H5 DNA (nt) + 2× Adjuvant 02 | 10 | 2 | 2.6 | 9 | 45.3 |
| T09 | AIV H5 DNA (nt) + 4× Adjuvant 03 | 9 | 2 | 2.7 | 7 | 17.3 |
| T10 | AIV H5 DNA (nt) + 2× Adjuvant 03 | 10 | 4 | 3.5 | 10 | 32.0 |
| T11 | AIV H5 DNA (nt) + 4× Adjuvant 05 | 10 | 3 | 2.8 | 10 | 59.7 |
| T12 | AIV H5 DNA (nt) + 2× Adjuvant 05 | 10 | 5 | 4.0 | 10 | 78.8 |
| T13 | AIV H5 DNA (nt) + 4× Adjuvant 06 | 10 | 0 | 2.0 | 8 | 21.1 |
| T14 | AIV H5 DNA (nt) + 2× Adjuvant 06 | 10 | 0 | 2.0 | 8 | 17.1 |

The results of this investigation provide evidence that the vaccines, utilizing the adjuvants of the present disclosure provide protection as determined by the hemagglutination inhibition titers using a range of adjuvant component concentrations and ratios as described in Example 1. In this study the neither the DNA nor adjuvant was treated with Ca++ or any divalent cation, therefore, divalent cations are is not required for efficacy. The adjuvant formulation 05 gave was optimal in this study for eliciting the highest immune response as measure by HAI antibody response. Furthermore, the adjuvant formulations used in this study provided the same kind of result as seen for the study done with IM inoculation (Example 3) in that all birds seroconverted after two doses. This indicates that all birds that were primed with a single dose (with a low concentration of DNA) and would likely be protected from challenge after a single dose. Additionally, the vaccine in the study does not have to be given IM when formulated in this manner, repeat doses are not necessary to immunologically prime the birds, and only very low doses of plasmid DNA are needed when using the adjuvants of the present disclosure. Most significantly, neither the delivery vehicle (the adjuvant) nor the DNA need to be treated with divalent cations, specifically Ca++, for efficacy.

Example 6

This example illustrates a comparative study with a minimum immunizing dose of 30 ug and stability of DNA vaccination administered intramuscularly or subcutaneously using the adjuvants of the present disclosure. The study measured the adjuvants ability to elicit an immune response in specific pathogen free chickens.

Materials and Methods

The chickens were 2 weeks at the time of the study initiation. 100 birds were used and blood was collected on Day 24 of the study.

The study design is below in TABLE 25.

TABLE 25

Study Design

| Trt Group[1] | Treatment Group Descriptions: Description | DNA (ug/dose) | Route[2] | No. of Chickens | Dose (ml)[3] | Day |
|---|---|---|---|---|---|---|
| T01 | Placebo - PBS | N/A | SC | 10 | 0.4 | 0, 14 |
| T02 | NT AIV H5 DNA[5] + 2× Adjuvant 03 | 30 | IM | 10 | 0.4 | 0, 14 |
| T03 | NT AIV H5 DNA[5] + 2× Adjuvant 03 | 30 | IM | 10 | 0.4 | 0, 14 |
| T04 | NT AIV H5 DNA[5] + 2× Adjuvant 03 | 30 | SC | 10 | 0.4 | 0, 14 |
| T05 | NT AIV H5 DNA[5] + 2× Adjuvant 03 | 60 | SC | 10 | 0.4 | 0, 14 |
| T06 | NT AIV H5 DNA[5] + 2× Adjuvant 05 | 30 | IM | 10 | 0.4 | 0, 14 |
| T07 | NT AIV H5 DNA[5] + 2× Adjuvant 05 | 60 | IM | 10 | 0.4 | 0, 14 |
| T08 | NT AIV H5 DNA[5] + 2× Adjuvant 05 | 30 | SC | 10 | 0.4 | 0, 14 |
| T09 | BBL AIV H5 DNA[4] + 2× Adjuvant 05 | 30 | IM | 10 | 0.4 | 0, 14 |
| T10 | Stability Prep - (AIV H5 DNA(bbl)[4] + 2× Adjuvant 05)[6] | 30 | IM | 10 | 0.4 | 0, 14 |

[1]For this study, the treatment group (TG) designation will identify the chickens and the test article.

[2]SC—Subcutaneous injection; IM—Intramuscular.

[3]Each chicken will be inoculated with a total of 0.4 mL (1 site 0.4 mL/SC and 2 sites 0.2 mL each/breast)

[4]BBL plasmid

[5]NT plasmid

[6]Stability sample

Note:

Treatment groups 02, 06, 07, 09, and 010 were done with calcium precipitated DNA.

TABLE 26

| Study Timeline | |
|---|---|
| Day | Activity |
| Day −35 | Set eggs/hatch |
| Day −14 | Place birds into cages (random) |
| Day −7 | Separate 10 birds/cage (1 cage/group) and tag/Daily Clinical Observations/Acclimation |
| Day 0 | Test Article Administration |
| Day 14 | Blood Collection<br>Test Article Booster Administration |
| Day 28 | Blood Collection |
| Days 0-28 | Daily Clinical Observations |
| Day 28 | End of Study |

Randomization and Acclimation

Birds were randomly placed in study cages in the order that they hatched (Day −14), 20-25 birds per cage. At 1-week of age (Day −7), birds were separated to at least ten birds per cage, one cage per treatment group. Birds were then individually tagged for identification. Bird receipt, tag identification and placement into cages were then documented.

Daily health observations were recorded on all study birds during the acclimation phase. Birds were acclimated for a minimum of three days. Clinical observations were performed daily and recorded.

Administration Route

Birds were administered the test articles either by intramuscular injection into the left and right sides of the breast or by subcutaneous injection in a single site in the back of the neck.

Test Article Administration—Days 0 and 14

On Day 0, 2-week old birds were examined for normal health and appearance and enrolled in the study. One cage represented one treatment group.

At least ten birds in T01 were inoculated by subcutaneous injection with PBS to serve as the negative control. At least ten birds in treatment groups T02, T03, T06, T07, T09, and T10 were inoculated with the appropriate test article by intramuscular injection on day 0 and day 14 of the study. The remaining treatment groups T04, T05, and T08 were inoculated with the appropriate test article by subcutaneous injection on day 0 and 14 of the study.

Health Observations and Adverse Events

Following administration of the test articles, clinical observations were recorded at least once daily until the end of the study (day 28).

Sample Collection and Testing

Blood was collected from each bird prior to the day 14 booster administration of test articles and day 28 according to site procedures. Blood was allowed to clot and then centrifuged to collect serum. The serum was stored at 2-7 or −18±5° C. until tested and stored long term at −18±5° C. Serum was assayed for the level of seroconversion via Hemagglutination Inhibition Assay (HAI).

Serum samples were assayed for seroconversion via HAI. The HAI titer was determined for each serum sample in each treatment group. The HAI titers of the birds inoculated with 30 ug DNA/dose (T04 and T06) were compared to the titers of the birds inoculated with 60 ug DNA/dose (T05 and T07) to determine the minimum immunizing dose. The HAI titers of birds inoculated with freshly prepared test article (T09) were compared to the titers of birds inoculated with retention sample (T10) to determine the stability of the vaccine.

The HAI titers of birds in other treatment groups were compared between each other to determine the efficacy of the adjuvant (T02 v T06 and T04 v T08), the plasmid (T06 v T09), the route (T03 v T04), or calcium precipitation (T02 v T03).

Descriptive statistics were used when appropriate to determine effectiveness of all treatment groups were compared to the negative control. Geometric means and statistical significance were determined by performing two-tailed Student's t-test or other appropriate method.

Test Articles

AIV H5 Plasmid DNA (bbl); Tested for purity and quality.

AIV H5 Plasmid DNA (nt); Tested for purity and quality.

Dulbecco's Phosphate Buffered Saline (DPBS); Cellgro, catalog: 21-031-CV

TABLE 27

| Adjuvant Stock Identification | |
|---|---|
| Adjuvant from Example 1 | Manufacturer |
| Adjuvant 03 2× | BBL |
| Adjuvant 05 2× | BBL |

TABLE 28

| Test Article Formulation for each Treatment Group | | | | |
|---|---|---|---|---|
| | Final Concentration of Components in Test Articles[1] | | | |
| Trt Group[3] | BBL AIV H5 Plasmid DNA per 0.4 ml dose | NT AIV H5 Plasmid DNA per 0.4 ml dose | 03 | 05 |
| T01[4] | | | | |
| T02 | | 30 ug | 2× | |
| T03 | | 30 ug | 2× | |
| T04 | | 30 ug | 2× | |
| T05 | | 60 ug | 2× | |
| T06 | | 30 ug | | 2× |
| T07 | | 60 ug | | 2× |
| T08 | | 30 ug | | 2× |
| T09 | 30 ug | | | 2× |
| T10[5] | 30 ug | | | 2× |

[1]Adjuvant stock concentrations are 5.0× per Example 1. Vaccines will be formulated at 2× concentration of the adjuvants.

[3]Vaccine prepared for T02, T06, T07, T09, T10 (retention) will use calcium precipitation; remaining will not use calcium precipitation

[4]T01 will receive 0.4 mL of PBS - SC

[5]T10 is retention sample T12 from NBHO2502

Results and Conclusions

TABLE 29

| Serology and GMT data at Day 13 and 28 | | | | |
|---|---|---|---|---|
| Group | # sero+ | GMT | # sero+ | GMT |
| NT AIV H5 DNA + 2× Adjuvant 03 | 0 | 2.0 | 0 | 2.0 |
| NT AIV H5 DNA + 2× Adjuvant 03 | 8 | 5.4 | 9 | 219.5 |
| NT AIV H5 DNA + 2× Adjuvant 03 | 4 | 3.4 | 9 | 348.4 |
| NT AIV H5 DNA + 2× Adjuvant 03 | 0 | 2.0 | 9 | 69.1 |
| NT AIV H5 DNA + 2× Adjuvant 05 | 5 | 3.7 | 9 | 101.6 |
| NT AIV H5 DNA + 2× Adjuvant 05 | 6 | 4.3 | 9 | 322.5 |
| NT AIV H5 DNA + 2× Adjuvant 05 | 8 | 8.6 | 9 | 512.0 |
| BBL AIV H5 DNA + 2× Adjuvant 05 | 2 | 2.9 | 9 | 80.6 |
| Stability Prep - (AIV H5 DNA(bbl) + 2× Adjuvant 05) | 5 | 5.0 | 9 | 188.1 |
| NT AIV H5 DNA + 2× Adjuvant 03 | 4 | 4.0 | 7 | 94.1 |

This study illustrates that the adjuvants of the present disclosure go against what is taught in the art, namely, that high amounts of DNA are needed, repeat doses are needed, adequate yields are not available for manufacturing, and that a high level of purity is needed. Further, it is thought in the art that Ca++ is required for DNA vaccines and that cationic delivery vehicles are needed for DNA vaccines. This study provides evidence that the adjuvants of the present disclosure do not require Ca++ or a cationic delivery vehicle in order to be effective and shelf-stable. Further, the preparation of the plasmid DNA using the adjuvants of the present disclosure can be made in grams/L as opposed to mg/L, giving a greater capacity for yield. The purification methods have also been streamlined by the present disclosure, as evidenced in this example. The adjuvants of the present disclosure have been shown to be microgram level in all species tested. The dose and yield optimization have lowered the COGs (Cost of Goods) by 10,000 to 100,000 times.

Example 7

This example illustrates the stability of DNA in adjuvant of the present disclosure for at least 18 months.

Materials and Methods

A plasmid, Poultry Adjuvant 01 P1/Tris-HCL Buffer was produced and stored at 2-7° C. This plasmid DNA is a CCCS DNA, which is purified from bacterial fermentation. The purification process provides for DNA in the preparation that is over 85% CCSC DNA, however linear DNA (L DNA) and relaxed circular DNA (RC), make up the balance of the purified DNA. The stability was measured at time points 0 days, 2 months, 6 months, 12 months, and 18 months both quantitatively by measuring the $A_{260}$ between samples incubated in buffer alone or with adjuvant of this disclosure. The DNA was qualitatively evaluated for CCCS, L, and RC DNA by agarose gel electrophoresis using DNA samples extracted from treated samples.

Specifically, the plasmid DNA was diluted to the appropriate concentrations using 10 mM Tris HCl, pH 8. There buffer contained no cationic salts or buffers (specifically Magnesium, Mangenese, or Calcium). The sample preparation for the study was done in a volume of 2000 ul by adding 480 ul of plasmid stock at 2 mg/ml, 1120 ul of 10 mM Tris HCl buffer, 400 ul of adjuvant stock (4× Adjuvant 01, per Example 1). The control sample was made in identical manner except the adjuvant component was substituted with 10 mM Tris HCL buffer. The plasmid DNA was not treated with Calcium or other cations prior to addition to the adjuvant test mixture. The plasmid DNA was covalently closed supercoiled (CCSC) DNA preparation, which is standard for plasmid preparation made by the method described above or methods of similar or equivalent procedure.

Test samples were stored at 2-7° C. for duration of the study. The adjuvant was produced and then the plasmid DNA was added to the adjuvant 6 months after manufacturing, two year stability data will be completed in the future.

At time 0, 2 months, 6 months, 13 months, and 18 months samples were removed from the incubation mixture with or without adjuvant and evaluated for stability of CCSC DNA.

The DNA is bound to the adjuvant and cannot be recovered without extraction with chloroform, the procedure for extracting the DNA from the adjuvant and buffer is known in the art.

Results and Conclusion

Figure 2:
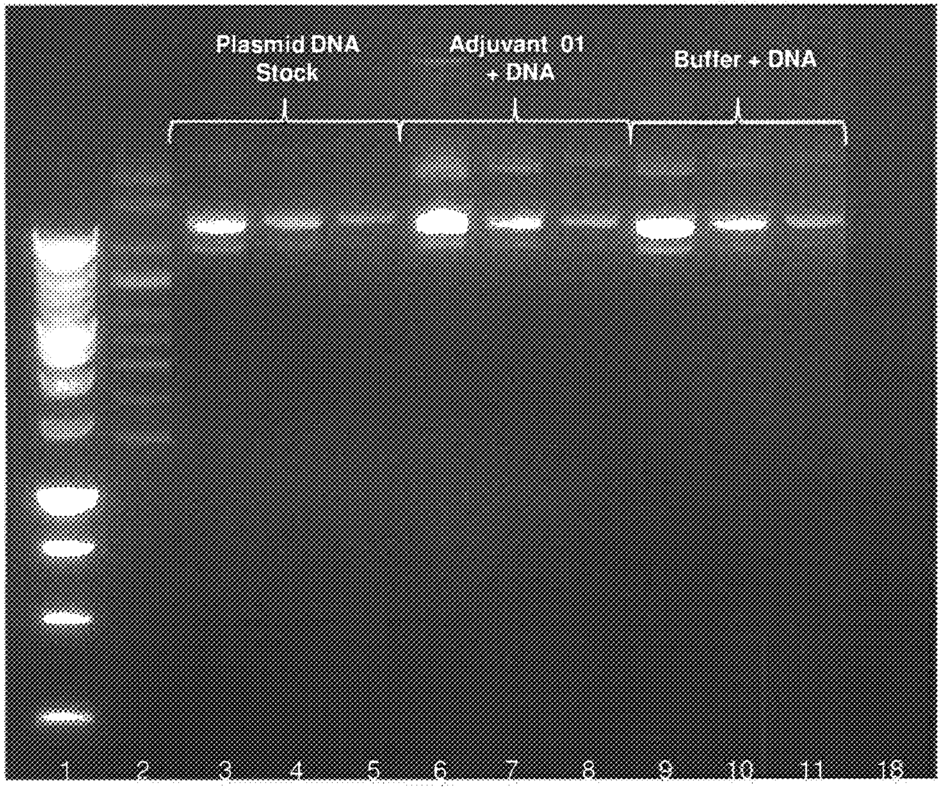
FIG. 2 is a photograph of a gel illustrating the qualitative demonstration of retention of double stranded covalently closed DNA recovered from extracted samples, where no degradation of DNA is observed after 18 months of incubation with the adjuvant of the present disclosure.

The results indicate that circular covalently closed supercoiled DNA (CCSC-DNA) which is the basis for most DNA or Gene therapy vaccines is stable in the adjuvants subject of this disclosure. The CCSC-DNA used in this study was stable for over 18 months when stored at 2.7° C. Liposomal preparations derivatized with Ca++ are not stable and cannot be stored for long periods of times after being suspended in aqueous solution with DNA. Adjuvant prepared from the present disclosure and combined with purified CCSC-DNA can be stable for over 18 months when suspended in liquid form. Furthermore, because the preparation used in this study also contain linear DNA and relaxed circular DNA as part of the purified preparation, the adjuvant-DNA preparations of these forms of DNA are also stable when placed in the adjuvant of the present disclosure (FIGS. 1 and 2). Thus, delivery of Ca++ treated DNA or Ca++ derivatized liposomes or other vehicles are not needed to gain effective vaccination or delivery of DNA when using adjuvants of the present disclosure, which is a clear addition and advantage to the art.

Example 8

This study illustrates stability of adjuvant/protein formulations (bovine serum albumin-BSA) when and incubated at refrigerated or ambient temperatures for at least 18 months.

Materials and Methods

The purpose of this study was to perform long term stability evaluation (12 months) of bovine serum albumin (BSA) combined with two different embodiments of the adjuvants of the present disclosure. The stability of the stored test articles (stored at 2-7° C. or 18-27° C. for 12 months ±4 weeks) were measured by seroconversion in CF-1 mice. The level of seroconversion in mice produced by the stored test articles were compared to that produced by fresh test articles prepared on day 0 and at the end of 18-months for this study. The fresh test articles were prepared using BSA that had been stored at −80±10° C., PBS that has been stored at 18-27° C., and the two adjuvant formulations that have been stored at either 2-7° C. or 18-27° C.

The stored test articles were originally prepared and inoculated into mice on the same day for the time 0 portion of this stability study. These stored test articles were inoculated again into mice after approximately 6 months of storage. In continuation of the stability study, these stored test articles were inoculated into mice again after 12 months of storage, 18 months and 24 months in the manner described in this protocol. However, the frequency and duration of testing subsequent to the 18 month time point was contingent on the results obtained in this study.

The primary objective of this study was to assess the stability of BSA combined with two different adjuvant formulations of the present disclosure by inoculating them into mice after approximately 18 months of storage at either refrigerated or ambient temperatures. The serological responses of the mice inoculated in this study were compared to the responses obtained in mice inoculated with test articles prepared fresh for this 12 month time point. The serological responses obtained in this study were also compared to those obtained during the two previous stability time points, time 0 and 6 month.

This protocol is separated into two major sections. The first section contains a description of the test articles being stored for stability, the preparation of the fresh test articles to be tested in this study and an overview of the two-year stability testing schedule. The second section describes the clinical phase for this protocol; future testing dates will have separate protocols for the clinical phase. The first section will be common among the testing dates.

Two different adjuvant formulations were combined with BSA for a target concentration of 50 ug BSA/dose. All test articles prepared were aseptically aliquoted into sterile glass vials with rubber stoppers and crimped shut.

Test article PBO/cold was prepared by aliquoting commercial phosphate buffered saline (PBS) into vials as described and stored at refrigerated temperature. Test articles BSA/PBS/RT and BSA/PBS/cold were prepared by adding 0.25 parts BSA and 1 part PBS for a target concentration of 500 ug/ml (50 ug/0.1 mL dose) and stored at ambient or refrigerated temperatures. Test articles BSA/Adj01/RT and BSA/Adj01/cold were prepared by adding 0.25 parts BSA and 1 part 5× Adjuvant 01 (Example 1) for a target concentration of 500 ug/ml (50 ug/0.1 mL dose) and stored at ambient or refrigerated temperatures. Test articles BSA/Adj06/RT and BSA/Adj06/cold were prepared by adding 0.25 parts BSA and 1 part 5× Adjuvant 06 (Example 1) for a target concentration of 500 ug/ml (50 ug/0.1 mL dose) and stored at ambient or refrigerated temperatures. Preparation of the stability test articles is summarized below.

TABLE 30

Summary of Stability Test Articles

| Test Article ID[1] | True Name[2] | Manufacturer | Storage Temp | Volume/ Vial (mL) | Number of Vials Prepared | Stability Testing Dates (month) | 12 Month Trt Group |
|---|---|---|---|---|---|---|---|
| PBO/cold | S-Placebo (PBS only) | Cellgro (Cat 21-031-CV) | 2-7° C. | 5 | 25 | 0, 6, 12, 18, 24 | T01 |
| BSA/PBS/cold | S-50 ug BSA + PBS | BBL | 2-7° C. | 5 | 26 | 0, 6, 12, 18, 24 | T02 |
| BSA/PBS/RT | S-50 ug BSA + PBS | | 18-27° C. | 5 | 26 | 0, 6, 12, 18, 24 | T03 |
| BSA/Adj01/cold | S-50 ug BSA + Adjuvant 01 4× | | 2-7° C. | 5 | 26 | 0, 6, 12, 18, 24 | T04 |
| BSA/Adj01/RT | S-50 ug BSA + Adjuvant 01 4× | | 18-27° C. | 5 | 26 | 0, 6, 12, 18, 24 | T05 |
| BSA/Adj06/cold | S-50 ug BSA + Adjuvant 06 4× | | 2-7° C. | 5 | 26 | 0, 6, 12, 18, 24 | T06 |
| BSA/Adj06/RT | S-50 ug BSA + Adjuvant 06 4× | | 18-27° C. | 5 | 26 | 0, 6, 12, 18, 24 | T07 |

[1]The remaining volume from each aliquot used to inoculate on days 0 and 14 of this 12-month study will be destroyed on day of use; the remaining retention aliquot will be retained.
[2]4× adjuvant samples were prepared from 5× stock adjuvant per Example 1.

Fresh Test Articles

Bovine Serum Albumin (BSA) 625 ug/ml freezer stock, BBL

Dulbecco's Phosphate Buffered Saline (DPBS); Cellgro, catalog: 21-031-CV Lot: 21031424

TABLE 31

Study Design

| Trt Grp | True Name[1] | Descriptor[2] | Storage Temperature |
|---|---|---|---|
| T01 | S-Placebo (PBS only) | S-PBS/cold | 2-7° C. |
| T02 | S-50 ug BSA + PBS | S-BSA/cold | 2-7° C. |
| T03 | S-50 ug BSA + PBS | S-BSA/RT | 18-27° C. |
| T04 | S-50 ug BSA + Adjuvant 01 | S-BSA + 01/cold | 2-7° C. |
| T05 | S-50 ug BSA + Adjuvant 01 | S-BSA + 01/RT | 18-27° C. |
| T06 | S-50 ug BSA + Adjuvant 06 | S-BSA + 06/cold | 2-7° C. |
| T07 | S-50 ug BSA + Adjuvant 06 | S-BSA + 06/RT | 18-27° C. |

[1]500 ug/ml BSA stock, 50 ug BSA/dose
[2]Descriptor for each treatment group

TABLE 32

Fresh Test Article Descriptions

| | | | Storage Temperature[3] | | |
|---|---|---|---|---|---|
| Trt Grp | True Name[1] | Descriptor[2] | BSA | PBS | Adjuvant |
| T08 | F-50 ug BSA + PBS | F-BSA | −80 ± 10° C. | 18-27° C. | |
| T09 | F-50 ug BSA + Adjuvant 01 | F-BSA + 01/cold | | | 2-7° C. |
| T10 | F-50 ug BSA + Adjuvant 01 | F-BSA + 01/RT | | | 18-27° C.[4] |
| T11 | F-50 ug BSA + Adjuvant 06 | F-BSA + 06/cold | | | 2-7° C. |
| T12 | F-50 ug BSA + Adjuvant 06 | F-BSA + 06/RT | | | 18-27° C.[4] |

[1]500 ug/ml BSA stock, 50 ug BSA/dose
[2]Descriptor for each treatment group
[3]Storage temperature of components used to prepare fresh test articles
[4]5.0× Adjuvant stocks stored in the same storage location and temperature as the stability samples stored at 18-27° C.

TABLE 33

Clinical Study Design

| Trt Grp[1] | Descriptor | Route[2] | No. Mice | Dose (mL) | Inoculation (Day) | Blood Collection (Day) |
|---|---|---|---|---|---|---|
| T01 | S-PBS/cold | SC | 5 | 0.1 | 0, 14 | 13, 28 |
| T02 | S-BSA/cold | SC | 10 | 0.1 | 0, 14 | |
| T03 | S-BSA/RT | SC | 10 | 0.1 | 0, 14 | |
| T04 | S-BSA + 01/cold | SC | 10 | 0.1 | 0, 14 | |
| T05 | S-BSA + 01/RT | SC | 10 | 0.1 | 0, 14 | |
| T06 | S-BSA + 06/cold | SC | 10 | 0.1 | 0, 14 | |
| T07 | S-BSA + 06/RT | SC | 10 | 0.1 | 0, 14 | |
| T08 | F-BSA | SC | 10 | 0.1 | 0, 14 | |
| T09 | F-BSA + 01/cold | SC | 10 | 0.1 | 0, 14 | |
| T10 | F-BSA + 01/RT | SC | 10 | 0.1 | 0, 14 | |
| T11 | F-BSA + 06/cold | SC | 10 | 0.1 | 0, 14 | |
| T12 | F-BSA + 06/RT | SC | 10 | 0.1 | 0, 14 | |
| Additional[3] | Baseline | N/A | 20 | N/A | N/A | ** |

[1]For this study, the treatment group (TG) designation will identify the mice and the test article. All adjuvants were at 4× concentration per description in Example 1.
[2]Mice will be inoculated via subcutaneous injection dorsal, between the shoulders
[3]Additional mice NOT inoculated with test article; used to obtain baseline blood samples
** Blood will be collected from the baseline mice as needed to obtain prescreen serum for use in the ELISA; no more than 10% of the total blood volume based on the average weight of the mice will be collected within a 3-4 week period.
F = Fresh;
S = Stability sample

TABLE 34

| STUDY TIMELINE | | |
|---|---|---|
| Day | Activity | Data Capture Forms |
| Days −6 to −8 | Daily Clinical Observations | SOP AC-004, Appendix II |
| Prior to day 0 | Blood collection (baseline mice only) mice bled one time within this period to obtain prescreen samples for confirmation of mice seronegativity via ELISA | Appendix II, Form 2 |
| Day 0 | Treatment Administration | Appendix II, Form 1 |
| Day 1-28 | Blood collection (baseline mice only) mice bled periodically during this time to obtain baseline blood samples | Appendix II, Form 2 |
| | Daily Clinical Observations | Appendix II, Form 3 |
| Day 13 | Blood collection | Appendix II, Form 2 |
| Day 14 | Treatment Administration | Appendix II, Form 1 |
| Day 28 | Blood collection | Appendix II, Form 2 |

Administration Route

All mice will be administered the test article via subcutaneous injection, dorsal between the shoulders.

Prescreen Sample Collection—Day −4-0 (Baseline mice only)

Blood was collected and pooled from the baseline mice (the mice not used in the study) once prior to day 0 of the study to obtain prescreen serum. No more than 10% of the total blood volume based on the average weight of the mice was collected. Blood collection was documented. Blood was allowed to clot and then centrifuged to collect serum. The serum was then pooled and stored at 2-7° C. or -18±5° C. until tested via ELISA to ensure the mice to be used in the study were seronegative to BSA.

Treatment Administration—Day 0

Mice will be examined for normal health and appearance and enrolled in the study. Each cage represented a treatment group and individual mice within each cage will be ear notched for identification purposes.

On day 0 of this study, one vial of each treatment group preparation was aseptically divided into three aliquots. One aliquot was administered to the mice immediately (Day 0). One aliquot was stored at 2-7° C. until administered to the mice on Day 14. The last aliquot was maintained at 2-7° C. as a retention sample. All treatment group preparations (for each TG) were administered to mice subcutaneously dorsal between the shoulders. The treatment administration was documented.

Sample Collection—Day 1-28 (Baseline mice only)

Blood was collected and pooled from the baseline mice (the mice not used in the study) as needed between days 1 and 28. No more than 10% of the total blood volume based on the average weight of the mice was collected within a 3-4 week period. Blood collection was documented. Blood was allowed to clot and then centrifuged to collect serum. The serum was then pooled and stored at 2-7° C. or −18±5° C. until used as a negative control in the ELISA.

Sample Collection and Testing

Blood was collected from each inoculated animal on days 13 and 28. No more than 10% of the total blood volume based on the average weight of the mice was collected within a 3-4 week period. Blood collection were documented. Blood was allowed to clot and then centrifuged to collect serum. The serum was then stored at 2-7° C. or −18±5° C. until tested. Serum was assayed for the level of seroconversion via ELISA.

Tissue samples were harvested from euthanized animals for histological observations. Tissues were fixed in 10% neutral buffered formalin or directly frozen.

Health Observations and Adverse Events

Clinical observations were recorded daily following test article administration, as indicated in the study timeline.

Assessment of Analysis/Data Analysis

Serum samples were assayed for seroconversion via ELISA. The level of antibody production in each serum sample for each treatment group was determined. Antibody production in the mice administered Adjuvant+BSA were compared to the antibody production in mice administered BSA+PBS. Antibody production in mice administered the various adjuvant formulations were compared between each other. Antibody production in the mice administered test articles that have been stored for stability analysis were compared to the mice administered test articles prepared fresh on day 0 of this study.

Antibody production levels in mice inoculated in this study were compared to the antibody levels produced.

Descriptive statistics were used when appropriate to determine effectiveness of all treatment groups compared to the negative control (PBS only). Geometric means and statistical significance were determined by performing two-tailed Student's t-test or other appropriate method.

Test Article Preparation

TABLE 35

| Preparation Summary of the Fresh Treatment Groups to be Prepared on Day 0 | | | | | | | |
|---|---|---|---|---|---|---|---|
| | | Final Concentration of Components in Test Articles[1] | | | | | |
| Trt Group | Descriptor | BSA[2] | PBS | Adj 01 2-7° C. | Adj 01 18-27° C. | Adj 06 2-7° C. | Adj 06 18-27° C. |
| T08 | F-BSA | 500 ug/ml | 0.2× | | | | |
| T09 | F-BSA + 01/cold | 500 ug/ml | | 4.0× | | | |
| T10 | F-BSA + 01/RT | 500 ug/ml | | | 4.0× | | |

TABLE 35-continued

Preparation Summary of the Fresh Treatment Groups to be Prepared on Day 0

| Trt Group | Descriptor | Final Concentration of Components in Test Articles[1] BSA[2] | PBS | Adj 01 2-7° C. | Adj 01 18-27° C. | Adj 06 2-7° C. | Adj 06 18-27° C. |
|---|---|---|---|---|---|---|---|
| T11 | F-BSA + 06/cold | 500 ug/ml | | | | 4.0× | |
| T12 | F-BSA + 06/RT | 500 ug/ml | | | | | 4.0× |

[1]Test articles were only be tested in this study; none were stored for subsequent stability studies. All adjuvants were at 4× concentration derived from 5× stocks in accordance with the description in Example 1.
[2]BSA (625 ug/ml) freezer stock stored at −80 ± 10° C.

Results and Conclusions

TABLE 36

Immune response to BSA by ELISA measurements after 12 months of storage.

| Treatment Group | Descriptor | 12 Month Day 13 Geometric Mean[1] | Incidence | 12 Month Day 28/29 Geometric Mean[1] | Incidence |
|---|---|---|---|---|---|
| T01 | S-PBS/cold | 10 | 0/5 | 20 | 0/5 |
| T02 | S-BSA/cold | 15 | 2/9 | 86 | 5/10 |
| T03 | S-BSA/RT | 25 | 5/10 | 184 | 7/10 |
| T04 | S-BSA + 01/cold | 2,828 | 10/10 | 34,297 | 10/10 |
| T05 | S-BSA + 01/RT | 806 | 10/10 | 18,839 | 10/10 |
| T06 | S-BSA + 06/cold | 5,657 | 10/10 | 29,857 | 10/10 |
| T07 | S-BSA + 06/RT | 5,657 | 10/10 | 21,112 | 10/10 |
| T08 | F-BSA | 20 | 5/9 | 149 | 7/10 |
| T09 | F-BSA + 01/cold | 2,144 | 10/10 | 11,189 | 10/10 |
| T10 | F-BSA + 01/RT | 1,866 | 10/10 | 12,996 | 10/10 |
| T11 | F-BSA + 06/cold | 3,732 | 10/10 | 48,503 | 10/10 |
| T12 | F-BSA + 06/RT | 3,031 | 10/10 | 24,251 | 10/10 |
| T13 | F-BSA + 01/EXP | 1,625 | 10/10 | 16,000 | 10/10 |

[1]Any Geometric Mean >20 is considered positive
*Normalized to respective BSA only GMT value
All adjuvants were at 4× concentration in accordance with the description in Example 1.

The results indicate that the adjuvants of the present disclosure were stable over a 12 month period when incubated with and without protein samples, which in this case was BSA. As can be seen from the data, all of the samples of adjuvant 06 were stable as measured by efficacy of immune response when inoculated into mice at 12 months whether stored at room temperature or under ambient conditions. This data suggest that the adjuvants can be incubated with antigen in liquid form without losing efficacy which allows for the ease of shipping, storage, and the use of the adjuvant either un-assembled or assembled with antigen. The data further indicates that the adjuvants would have an increased stability at elevated temperatures, which is most likely a contributing factor to the immune responsiveness in animals.

Example 9

This example illustrates a feature of the adjuvant formulations of the present disclosure, such as the fact that the adjuvant formulations of the present disclosure are stable at room temperature, and when refrigerated, Specifically, this stability study was designed to determine the stability of the adjuvants of the present disclosure stored at either ambient temperature or 2-7° C. for up to 24 months. This study illustrates the stability of the adjuvant formulation incubated at refrigerated or ambient temperatures for at least 12 months.

Materials and Methods

Adjuvants were filled in sterile PETG bottles (Nalgene, Wheaton, or equivalent) with sterile plastic closures.

Adjuvants enrolled in this stability were stored at either ambient temperature or 2-7° C. for up to 24 months. Two aliquots were pulled at each time point for analysis. Testing must be initiated within ±one week of the scheduled time point. Once pulled, all aliquots were stored at 2-7° C. until testing had been completed.

Appearance Testing

Adjuvant samples were tested for appearance in accordance with SOP XQC-087. In addition, each sample were examined for visible separation of the emulsion; the amount of separation present will be measured and documented at each time point.

Particle Size Analysis

Particle size analysis of adjuvant samples was performed.

pH Testing

Adjuvant samples will be tested for pH.

Viscosity Testing

Adjuvant samples will be tested for viscosity.

TABLE 37

Stability Plan
Stability Testing Conducted Per Lot

| Test | Months in Storage (2-7° C. or Ambient Temperature)[1] 3 | 6 | 9 | 12 | 15 | 18 | 21 | 24 |
|---|---|---|---|---|---|---|---|---|
| Appearance | x | x | x | x | x | x | x | x |
| Particle Size[2] | | | | x | | | | x |
| pH | | x | | x | | x | | x |
| Viscosity | | x | | x | | x | | x |

[1]Time 0 represents the original QC testing performed
[2]May or may not be performed at a given time point if other testing yields the expected value Results and Conclusions

TABLE 38

Results of the In Vitro Adjuvant Stability Study Adjuvant 06 4×.

| Test | Storage Conditions | Time 0 | 6 months | 12 months |
|---|---|---|---|---|
| Appearance | 2-7° C. | 3 | 3 | 3 |
| | RT | | 3 | 3 |
| Settling (mm clearing) | 2-7° C. | 0 | 0.5 | 1 |
| | RT | | 0.5 | 1 |

TABLE 38-continued

Results of the In Vitro Adjuvant Stability Study Adjuvant 06 4×.

| Test | Storage Conditions | Time 0 | 6 months | 12 months |
|---|---|---|---|---|
| pH | 2-7° C. | 7.13 | 7.13 | 7.15 |
| | RT | | 7.12 | 7.12 |
| Viscosity | 2-7° C. | 21 | 24 | 24 |
| (cST) | RT | | 23 | 24 |
| Mean particle | 2-7° C. | 0.62 | Not Done | 0.96 |
| size (microns) | RT | | | 0.80 |

TABLE 39

Results of the In Vitro Adjuvant Stability Study Adjuvant 03 4×.

| Test | Storage Conditions | Time 0 | 6 months | 12 months |
|---|---|---|---|---|
| Appearance | 2-7° C. | 2 | 2 | 2 |
| | RT | | 3 | 4 |
| Settling | 2-7° C. | 0 | 3 | 6 |
| (mm clearing) | RT | | 3 | 9 |
| pH | 2-7° C. | 6.91 | 6.93 | 6.95 |
| | RT | | 6.70 | 6.56 |
| Viscosity | 2-7° C. | 17 | 17 | 16 |
| (cST) | RT | | 19 | 20 |
| Mean particle | 2-7° C. | 0.81 | Not Done | 0.85 |
| size (microns) | RT | | | 1.37 |

This study shows biophysical properties stability of the adjuvants of the present disclosure for at least 12 months at cold temperature and at room temperature when store in liquid form.

TABLE 40

Data on pH, viscosity, and particle size; comparison of freeze-dried and non-freeze-dried samples.

| Test | Test Date | Adjuvant 01 4× | Adjuvant 02 4× | Adjuvant 03 4× |
|---|---|---|---|---|
| pH | Original | 7.11 | 7.11 | 7.11 |
| | | 7.09 | 7.10 | 7.09 |
| Viscosity | Original | 16 | 16 | 16 |
| (Cst) | @ 2 yr dating | 16 | 16 | 16 |
| | @ 2 yr dating Freeze Dried and Resuspended | 15 | 17 | 17 |
| Mean | Original | 0.86 | 0.78 | 0.77 |
| Particle Size | @ 2 yr dating | 0.82 | ND | ND |

This data makes it clear that three different adjuvant compositions of the present disclosure all show stability for at least 24 months in ambient temperature, when freeze-dried, and when resuspended after being freeze dried. For the 01 adjuvant formulation, the pH went from 7.11 to 7.09 with the 2 year dating, the viscosity stayed at 16, and the particle size went from 0.86 to 0.82. For the 02 adjuvant formulation and the pH went from 7.11 to 7.10 with the 2 year dating. For the 03 adjuvant formulation, the pH went from 7.11 to 7.09 with the 2 year dating and the viscosity stayed at 16. This is evidence of extended stability of the adjuvants of the present disclosure in different conditions which illustrates an advancement in the art when compared to previously known adjuvant formulations

Example 10

Material and Methods

Seventy one day old layer chicks were vaccinated with either 0.2 ml of the DNA vaccine given subcutaneously or with 0.2 ml of PBS. The DNA vaccine was a eukaryotic DNA vaccine plasmid backbone containing the HA gene from GyrFalcon/Washington/41088-6/2014. A total of 60 chicks were administered the DNA vaccine and 10 chicks were used as controls. At 2 weeks after the original vaccination, 20 chicks were boostered with 0.2 ml of DNA vaccine, and 20 chicks were vaccinated with 0.2 ml of the GyrFalcon/Washington/41088-6/2014 reverse genetics killed vaccine given with an adjuvant. Challenge was conducted when the birds were 4 weeks of age (2 to 4 weeks a weeks after the last vaccination) with A/Turkey/Minnesota/12582/2015 (H5N2) at a dose of $10^{6.5}$/EID50 administered in a dose of 0.5 ml by the choanal route of inoculation. The challenge virus was from a recent outbreak and the challenge dose was designed to give 1000 chicken lethal dose$_{50}$ as a stringent challenge. Each treatment group received 2× of adjuvant 05, calculated per Example 1.

Determination of Viral Shedding.

Oropharyngeal swab samples from chickens were suspended in 2 ml sterile brain heart infusion (BHI) broth (Sigma-Aldrich, St. Louis, Mo.) containing 1× antibiotic/antimycotic (Mediatech, Herndon, Va.), and frozen at −70° C. until RNA extraction. Total viral RNA from 250 ul of sample was added to Trizol and after the addition of chloroform the aqueous phase was used with the MagMAX-96 AI/ND Viral RNA Isolation Kit (Ambion, Inc., Austin, Tex.). The procedure for RNA isolation was carried out using the KingFisher magnetic particle processing system (Thermo Scientific, Waltham, Mass.).

Quantitative real-time RT-PCR (RRT-PCR) was performed using primers and probe specific for type A avian influenza matrix gene (2). The AgPath-ID RT-PCR Kit (Invitrogen, Carlsbad, Calif.) was used with eight μl of the RNA sample and nuclease-free water were added to make a final volume of 25 μl. The reverse transcription reaction consisted of one cycle of 30 min. at 50° C., followed by 15 min. at 95° C. Forty cycles of is denaturation at 94° C., followed by annealing for 20 s at 60° C. were carried out in the PCR reaction. Both reactions were carried out in a Smart Cycler II (Cepheid, Sunnyvale, Calif.) real-time PCR machine. The $EID_{50s}$ of virus from the swab samples were extrapolated from the cycle thresholds by using standard curves generated from the known amounts of RNA of the challenge viruses used (1). Detection limits of each RRT-PCR run were calculated based on the standard curve, by setting the cycle threshold values equal to the number of cycles run. For statistical purposes, samples that were RRT-PCR-negative in this study were assigned a cycle threshold value of 1 cycle below the lowest detection point in the standard curve.

A Hemagglutination inhibition (HI) test was then performed. Hemagglutination inhibition antibody titers against AIV were determined by using the HI test (3). Homologous beta-propiolactone-inactivated antigen (Ag) was diluted in PBS to make a concentration of four HA units. Homologous Ag refers to the A/gyrfalcon/Washington/41088-6/2014 H5N8 virus which is the same hemagglutinin gene as used in the RP vaccine except the RP gene was modified to have a low pathogenic cleavage site which does not affect the antigenicity of the virus. Fifty microliters of Ag were added per well of a 96-well plate, where test serum was two-fold, serially diluted. Plates were incubated for 15 min. at room temperature before 0.5% chicken red blood cells were added to each well. Plates were shaken for 15 s, and incubated for 45 min. at room temperature. Results were interpreted as the reciprocal of the last well that had complete inhibition of hemagglutinating activity. For statistical purposes a reciprocal titer of 4 was considered the lowest positive result.

Results and Conclusions

The vaccinated and control birds were challenged with A/Turkey/Minnesota/12582/2015 (H5N2) at 2 or 4 weeks after the last vaccination. All the control birds showed severe clinical disease or death by 3 days post-challenge with a Mean Death Time (MDT) of 2.1 days, and birds with severe clinical disease were euthanized and recorded as dead the following day as required under the IACUC protocols (FIG. 1).

Serology was conducted on blood taken at the day of challenge, 4 weeks of age and 2 or 4 weeks after vaccination. None of the control birds or the single DNA vaccinated birds had detectable HI antibody titers. Of the vaccinated birds, 7 of 20 birds had detectable antibody titers ranging from 4 to 32 in the twice DNA vaccinated group and 19 of 20 birds had titers in the DNA/RG group. The geometric mean titer for the birds that seroconverted were 8.8 ($2^{3.14}$) and 16.6 ($2^{4.05}$) respectively. (Table 26)

Viral shedding post-challenge. All the control birds died or were euthanized on day 3 post-challenge, but all birds, dead or alive, were oropharyngeally swabbed on day 2. All vaccinated birds were swabbed at day 2 and all remaining birds were sampled on day 4 post-challenge. The control birds on day 2 were shedding $10^{7.1}/EID_{50}$ with all birds shedding similar titers of virus. The single DNA vaccinated birds at day 2 were shedding $10^{6.6}/EID_{50}$, the double DNA vaccinated group were shedding $10^{5.4}/EID_{50}$ logs of virus, and the DNA/RG vaccinated group were shedding $10^{2.9}/EID50$ logs of virus respectively (FIG. 1). The amount of virus shedding was statistically different (P=<0.001) between the controls and twice DNA vaccinated group and the DNA/RG vaccinated birds on day 2 using the Mann-Whitney Rank Sum Test.

The prime boost vaccine approach of the DNA vaccine at a day of age and a booster at 2 weeks was 95% effective against challenge while the treatment group given the 2 dose DNA vaccine provided protection in 55% of the vaccinated birds. The correlation was extremely high that the birds that seroconverted on the HI test with at least a titer of 4 survived challenge and had reduced shedding. These results indicate that the DNA vaccine can be used in standalone or combination vaccination trials.

TABLE 41

Hemagglutination Inhibition Titers by individual vaccinated bird.

| | GMT |
|---|---|
| G1 Sham | 0 |
| G2 DNA vx/single | 0 |
| G3 DNA vx + DNA boost | 8.8 |
| G4 DNA vx + rgH5 boost 4 | 16.6 |

Hemagglutination Inhibition titers by individual vaccinated bird. The minimal positive HI titers was 4, so measured titers of 2 were converted to 0 for calculation. For geometric mean titers, the birds with negative titers were not included in the calculation.

Example 11

Efficacy Study for the Serological Assessment of DNA Vaccine Combined Adjuvant of the Present Disclosure in Turkeys The purpose of this study was to establish a reasonable expectation of efficacy for a High Pathology Avian Influenza (HPAI) DNA vaccine using the adjuvants of the present disclosure. This was accomplished by assessing the ability of the vaccine to elicit an immune response in turkeys. To this end, a plasmid DNA containing a modified gene for the high path avian influenza virus, A/gryfalcon/WA/41088-6/2014 H5N8, hemagglutinin (HA) protein was combined with VaxLiant adjuvants and administered via the subcutaneous and intranasal routes.

The modified plasmid, NTC8685-eRNA41H-KP307984.1-HA-Modified encodes the HA gene from highly pathogenic (HP) Avian Influenza Virus (AIV) strain A/gyrfalcon/Washington/41088-6/2014 (H5N8). The H5 sequence was modified to change the HP multibasic cleavage site (PLRERRRKRGLF) (SEQ ID NO. 1) to a monobasic cleavage site. The modified H5 gene was produced synthetically, cloned into the NTC8685-eRNA41H optimized eukaryotic expression vector, and the construct was transformed into the *E. coli* strain NTC4862.

Efficacy was measured by testing for seroconversion to the inactivated virus containing the unmodified HA gene using a hemagglutination inhibition assay.

Materials and Methods

ENABL 1 and 0.5×ENABL™ 5 with pHA DNA (IVP 1 and 2) or phosphate buffered saline (PBS) with pHA DNA (MPC), was administered subcutaneously (SC) in each bird. Each IVP treatment group included a minimum of 22 birds and the MPC group 10 birds, were inoculated on Day 0. Birds were observed for overall general health for the entire study. All birds were inoculated on study day 0. Blood was collected approximately 2 weeks after each inoculation and tested for seroconversion.

TABLE 42

Study Description

| TG | Description | Route[1] | No. of Birds | Vaccination (Day) | Blood Collection (Day) |
|---|---|---|---|---|---|
| T01 | PBS Control (MPC-1) | SC/base of neck | 10 | 0, 14 | 13, 28 (terminal) |
| T02 | pHA DNA + 0.5× ENABL 5 (IVP-1) | SC/base of neck | 22 | 0, 14 | 13, 28 (terminal) |

TABLE 42-continued

| Study Description | | | | | |
|---|---|---|---|---|---|
| TG | Description | Route[1] | No. of Birds | Vaccination (Day) | Blood Collection (Day) |
| T03 | pHA DNA + 0.5× ENABL 5 (IVP-1) | SC/base of neck | 22 | 0* | 21 |

[1]SC—subcutaneous at the base of the neck; IN—intranasal

TABLE 43

| Test Articles | | | |
|---|---|---|---|
| ID | Lot | Description per Dose | Lot Testing |
| MPC-1 | TBD | Phosphate Buffered Saline | N/A - commercial |
| IVP-1 | HA-060715-30BM13 | 30 ug pHA-hp5 with 0.5× ENABL | Purity and Identity |

TABLE 44

| Study Timeline | |
|---|---|
| Day | Activity |
| Day 0 | Day of Arrival<br>Test Article Administration |
| Day 13-14 | Blood Collection (T01, 02)<br>Test Article Booster Administration (T01, 02) |
| Day 21 | Blood Collection (T03) |
| Day 28 | Blood Collection (T01, 02, 03) |
| Days 0-28 | Daily Clinical Observations |
| Day 28 | End of Study, Bird reconciliation |

Administration Route. Birds were administered the test articles either by subcutaneous injection in the back of the neck, or intranasally dripped into the nares. The Test Article was administered at Days 0 and 14. The birds in T01 received PBS via the SC route and represent the MPC-1. The remaining birds were inoculated as described in the Study Design. On Day 14, birds in groups T01, 02 received product and this was the boost. Birds in groups T03 did not receive a boost.

Sample Collection and Testing. Blood was collected from each bird in groups T01, 02 prior to the day of booster administration of test articles and at the end of the study according to site procedures. Birds in groups T03 were bled on day 21 and at the end of the study. Blood was allowed to clot and then centrifuged to collect serum. The serum was stored at 2-7 or −18±5° C. Serum was assayed for the level of seroconversion via inhibition of 4-8 hemagglutination units of the virus, A/gyrfalcon/WA/41088-6/2014 H5N8 BEI per BBL SOP LP-054.

Results and Conclusions

Serum was assayed for the level of seroconversion via inhibition of hemagglutination of the virus, A/gyrfalcon/WA/41088-6/2014 H5N8 BEI inact, which contained the unmodified HA gene, per BBL SOP LP-054. The hemagglutination inhibition (HAI) titer was determined for each serum sample in each treatment group. Briefly, serial dilutions of the serum were incubated with 4-8 hemagglutinin units and finally added to chicken red blood cells. The HAI titer was reported as the inverse log of the last dilution where there is 100% inhibition of viral-specific hemagglutination in all replicates. The HAI titers in the birds administered the various adjuvant formulations were compared.

TABLE 45

| Results, Turkey Efficacy | | | | | | |
|---|---|---|---|---|---|---|
| | Turkey Efficacy, Day of hatch vaccination | | # birds | Vacci-nations | Blood Collection (day) | GMT HAI of sero-converted birds |
| T01 | PBS | SQ | 10 | primary (Day 0) | 14, 28 | 2 |
| T02 | 30 ug/0.2 mL, LP7, HPAI HA-mod (fresh) | SQ | 22 | primary (0), boost (14) | 14, 28 | 10.6 |
| T03 | 30 ug/0.2 mL, LP7, HPAI HA-mod (fresh) | SQ | 22 | primary (Day 0) | 21 | 2 |

ENABL LP7 ™ or LP7 ™ is a tradename for 2× concentration of Adjuvant 05

Results indicate that turkeys can be vaccinated with the HPAI DNA/adjuvant combination at one day of age. Furthermore, that birds seroconverting would be protected against homologous challenge with two dose regimen when administered SC with the formulation tested in this study.

Example 12

The adjuvant formulas of the present disclosure to be tested as the investigational veterinary products (IVPs) in this turkey study were ENABL® 1 and 6 formulated with a plasmid DNA (pHA) containing a modified hemagglutinin (HA) gene from a highly pathogenic (HP) Avian Influenza Virus (AIV) strain A/gyrfalcon/Washington/41088-6/2014 (H5N8). The H5 sequence was modified to change the HP multibasic cleavage site (PLRERRRKRGLF) (SEQ ID NO. 1) to a monobasic cleavage site. The modified H5 gene was produced synthetically, cloned into the NTC8685-eRNA41H optimized eukaryotic expression vector. The same pHA was mixed with phosphate buffered saline (PBS) to serve as the study's matched placebo control (MPC).

The purpose of this study was to establish a DNA vaccine withdrawal time of 21-days for turkeys inoculated with ENABL® 1 and ENABL® 6.

Materials and Methods

Study Design

ENABL 1 and ENABL™ 6 with pHA DNA (IVP 1 and 2) or phosphate buffered saline (PBS) with pHA DNA (MPC), was administered subcutaneously (SC) in each bird. Each treatment group consisted of a minimum of 10 birds inoculated on Day 0. Birds were observed for overall general health for twenty-one days. Site-specific observations were conducted on days 1 through 7, 14, and 21. All birds that were euthanized due to morbidity or found dead after Study Day 0 and before Day 21 were necropsied to determine if the death was a result of the IVP or MPC. All remaining birds on Day 21 had gross pathology and histological examinations. The study design is summarized in Table 46.

TABLE 46

| Study Description | | | |
|---|---|---|---|
| Treatment Group | Product* | Number of Birds | Necropsy and Sample Day |
| T01 | pHA DNA + ENABL ™ 1 (IVP-1) | 15 | 21 |
| T02 | pHA DNA + ENABL ™ 6 (IVP-2) | 15 | 21 |
| T03 | pHA DNA + PBS (MPC) | 15 | 21 |

All adjuvants were at 4x concentration per description in Example 1 ENABL ™ 1 is adjuvant 01 at 4x and ENABL ™ 6 is Adjuvant 06 at 4x per Example 1.
*Each product will be identified by the lot number assigned. A dose of 0.2 mL of the final products will be administered subcutaneously in the neck.

The test articles are described below. Prior to use in the study they were designated test article A through C, and identified as such during the study to maintain proper blinding.

TABLE 47

| pHA DNA, containing ENABL ® 1 (The Investigational Veterinary Product #1) | |
|---|---|
| True Name | Avian Influenza Vaccine, DNA, H5 Subtype |
| Formulation | 40% bulk pHA, 40% PBS and 20% ENABL ® 1 |
| Storage Conditions | 2 to 7° C. |
| Treatment Route | SC - Neck |
| Testing | Plasmid DNA identity |
| Requirements | Satisfactory for purity |
| Product Preparation | IVP-1 will be supplied ready to use |
| Applied Dose | 1 dose - 0.2 mL |

ENABL ™ 1 is a tradename for a commercially available adjuvant at 5x for the adjuvant in Example 1

TABLE 48

| pHA DNA, containing ENABL ® 6 (The Investigational Veterinary Product #2) | |
|---|---|
| True Name | Avian Influenza Vaccine, DNA, H5 Subtype |
| Formulation | 40% bulk pHA, 40% PBS and 20% ENABL ® 6 |
| Storage Conditions | 2 to 7° C. |
| Treatment Route | SC - Neck |
| Testing | Plasmid DNA identity |
| Requirements | Satisfactory for purity |
| Product Preparation | IVP-2 will be supplied ready to use |
| Applied Dose | 1 dose - 0.2 mL |

ENABL ™ 6 is a tradename for a commercially available adjuvant at 5x for Adjuvant 06.

TABLE 49

| pHA DNA + PBS (The Matched Placebo Control) | |
|---|---|
| True Name | Avian Influenza Vaccine, DNA, H5 Subtype |
| Formulation | 40% pHA DNA 60% PBS |
| Storage Conditions | 2 to 7° C. |
| Treatment Route | SC - Neck |
| Testing Requirements | Plasmid DNA identity<br>Satisfactory for purity |
| Product Preparation | MPC will be supplied ready to use |
| Applied Dose | 1 dose - 0.2 mL |

TABLE 50

| Study Timeline | |
|---|---|
| Study Day | Activity |
| Day 0 | Tag<br>Bird Health and Injection Site Evaluation<br>Product Administration |

TABLE 50-continued

| Study Timeline | |
|---|---|
| Study Day | Activity |
| Days 1-21 | General Clinical Observations |
| Days 1-7 | Injection Site Observation |
| Day 14 | Injection Site Observation |
| Day 21 | Injection Site Observation<br>Necropsy and Sample Collection |

Treatment Administration—Day 0

Health assessment, clinical observations, and proposed injection site observations were recorded the day of treatment. Each bird was injected once in the subcutaneous space in the mid part of the back of the neck with the designated product. Dose was 0.2 mL per site.

Clinical Observations, Injection Site Observations, and Adverse Events

All the birds were observed daily for overall health status following test article administration, as indicated in the study timeline. Clinical signs were categorized according to standardized low-level terms developed by the Veterinary Dictionary for Drug Regulatory Activities (VEDDRA).

Injection sites were palpated, observed and recorded on Days 1-7, and day 14. On day 21 a final injection site palpation and exam occurred of all injected sites just prior to euthanasia and necropsy.

Sample Collection

For histological data collection, tissue samples were harvested from the injection sites and surrounding tissue. The pathologist examined the injection site for gross lesions related to injection site abnormalities.

Injection Site Examination and Scoring

The injection site was palpated and findings recorded. The skin was incised and the underlying tissue examined. A score for the injection site was assigned during necropsy by the pathologist, based on presence of any drainage tract, abscessation, edema, hemorrhage, or necrosis. The most severe manifestation at any given injection site determined the single injection site score assigned by the pathologist to the injection site. In the event more than one manifestation is observed at a single injection site, the other (lower and non-score-determining) manifestations were recorded, but these less severe findings did not reduce the score assigned based on the most severe manifestation.

Injection Site Histological Scoring

Each tissue collected was examined for histological evidence of site reactions. As for the gross necropsy findings, the MOST SEVERE grade was assigned to the injection site and used as the histology score for the site.

Results and Conclusions

For each treatment group 14 birds survived the initial placement and study period that met the criteria inclusion in the study due to health status at the time of acclimation. The results of the site observations and gross/histopathology at necropsy are provided in the following table.

TABLE 51

| Results of Observations and Gross/Histopathology | | | |
|---|---|---|---|
| Treatment Group | Site Observations[1] | Gross Pathology at Injection site[2] | Histological (microscopic) examination at injection site[3] |
| Placebo control | 0 | 0 | 0 |
| T01 (pHA DNA + ENABL ™ 1 (IVP-1)) | 3/14 | 6/14 | 7/14 |
| T02 (pHA DNA + ENABL ™ 6 (IVP-2)) | 3/14 | 7/14 | 3/14 |

[1]Number of animals with visible swelling by end of the 21 day observation period

[2]Number of animals with noticeable inflammatory response at necropsy, mild to moderate.

[3]Number of animals with physiological response only observable microscopically at necropsy ENABL ™ 1 is a tradename for a commercially available adjuvant at 5x for the adjuvant in Example 1

Site observations. None of the placebo inoculated birds were scored for any abnormal responses either at the site observation or necropsy level all birds scored negative for any type of clinical manifestations for vaccine or injury related pathology. For treatment group T01 and T02 only 3 of 14 birds (6 birds total) demonstrated some swelling at the site of inoculation that could be palpated at the end of the 21 day period. The remaining birds (22 birds) were normal.

Necropsy. At necropsy the overall gross pathology observations for T01 group indicated that 6 of 14 birds had no type of lesion or pathology associated with injection site at 21 days, of the 8 remaining birds only two birds had more severe inflammatory response, the remaining were moderate to mild. The overall histological results indicated that 7 of 14 birds had no visible infiltration indicative of inflammation or immune response at 21 days. Of the remaining 7 birds, the observations were moderate. None of the birds had visible bruising or hemorrhage related injury at the site of injection.

The overall gross pathology observations for the T03 treatment group, 7 of 14 birds had no type of lesion or pathology associated with injection site at 21 days, the 7 birds remaining there were mostly mild responses. The overall histological results indicated that 3 of 14 birds had no visible infiltration indicative of inflammation or immune response at 21 days, while the remaining 11 birds indicated some mild to moderate infiltration indicative of immune response or inflammation.

The adjuvants tested here showed very little site reactions visible during the 21 day observation, the animals remained healthy and were not in any discomfort. Only on necropsy could any pathology be seen by trained pathologist, that were also evident in histology sections my microscopic examination. None of the reactions observed at 21 days (end of study) at necropsy by gross pathology would have been considered severe enough to disrupt slaughter line for poultry processing. All lesions that could be scored upon necropsy were mild to moderate and appeared to be resolving themselves indicating that within time (several days) the tissue would return to normal appearance. These results indicate that the adjuvant would be considered for 21 day withdrawal safety approval, which is the lowest time allowed by USDA for use of an adjuvant with a vaccine formulation.

Example 13

This study established a reasonable expectation of efficacy for the products and methods of the present disclosure. A high passage flu virus, namely, Avian Vaccine, H5 Subtype, DNA, was used. Serological testing in chickens using the vaccine was done using the adjuvant compositions of the present disclosure. All treatment groups were with 2× Adjuvant 05, ENABL™ LP7

Materials and Methods

A DNA vaccine was developed using DNA backbone plasmid NTC8685eRNA41H-KP307984.1. This plasmid backbone was used to carry a modified synthetic hemagglutinin (HA) gene encoding the HV antigen for the high pathogenic (HP) avian influenza virus, A/gyrfalcon/WA/41088-6/2014 (H5N8). The published H5 sequence was modified prior to the synthesis at its multibasic cleavage site to form a sequence that will express a H5 protein characteristic of the monobasic site of low pathogenic avian influenza viruses and this modification also introduced a unique restriction site for identification. The modified H5 gene was produced synthetically, cloned into the NTC8685-eRNA41H optimized eukaryotic expression vector, and the construct was transformed into the *E. coli* strain NTC4862 resulting in an *E. coli* master seed candidate carrying this modified plasmid. This *E. coli* was used to produce the master seed, Master Seed AIV H5 Mod, Lot# MS 16Jun15HPAIV (ML#171713).

Testing of the master seed, Lot# MS 16Jun15HPAIV, for purity and identity was completed and the CVB has approved its use for the production of vaccines (ML#171800). In addition, the methods to be used for vaccine production and testing were submitted to USDA APHIS CVB for approval. CVB has assigned the new product the true name Avian Influenza Vaccine, H5 Subtype, DNA, Product Code 1057.D0 for Antelope Valley Bios, Est. 419.

In this study, therefore, to determine the minimum dose where adequate seroconversion incidence could be assured, 3 graded dose levels of DNA in Code 1057.D0 serials were prepared and were tested for HAI response in groups of SPF chickens. In this study, two alternative schedules for vaccination were examined, administering the priming dose either at day of hatch or at 14 days of age.

Study Design

One hundred and eighty-five (185) chickens, Lot # AVB18Nov15, were hatched from Valo SPF eggs and were enrolled in the study. On day of hatch, healthy birds were transferred to the clinical site for enrollment.

One hundred and thirty-seven (137) of these healthy birds were placed on test at day of age (day of hatch). The day of age birds (0DA) were divided into one group of 6 birds (Group 1, the MPC group), one group of 21 [Group 2, (22 birds allotted but one bird was culled just prior to vaccination)] and 5 groups of 22 birds each (Groups 3-7). Groups 1-7 were housed in a total of 13 cages, 2 cages per group while Group 1 birds were housed in a single cage.

The remaining 47 birds were held in a single brooder room until 2 weeks of age when they were then divided into one group of 9 birds (Group 9, the PC group) and 2 groups of 18 birds each (Groups 10 and 11 IVP1 or IVP2, 14DA). Two birds were culled prior to study initiation so a total of 45 birds were placed on test. These birds were housed in 5 cages, 2 cages per Groups 10 and 11 and 1 cage for Group 9.

Administration Route

Birds were administered the test articles either by SQ injection in the nape of the neck, or IM in the breast muscle.

Timing of Test Article Administration

The 0DA vaccination groups 1-7 were administered the first test article dose on day of hatch (Study Day 0). The same birds received a booster dose of the respective test article on Study Day 14 (see Table 52).

The 14DA vaccination groups (Groups 9-11) were administered the test article on Study Day 14 and treated similarly on Study Day 28 (see Table 53).

TABLE 52

Treatment Descriptions, Day of Age (0 DA) Birds

| Group ID | Product[1] | Route | # of Birds | Dose | Vaccination, Study Days | Blood Collection, Study Days |
|---|---|---|---|---|---|---|
| 1 | MPC: DPBS | SQ | 6 | 0.2 mL | 0, 14 | 13, 28, 35 |
| 2 | IVP-1: 30 μg HP-AIV H5 mod | SQ | 21 | 0.2 mL | 0, 14 | 13, 28, 35 |
| 3 | IVP-2: 30 μg HP-AIV H5 mod | IM | 22 | 0.2 mL | 0, 14 | 13, 28, 35 |
| 4 | IVP-3: 10 μg HP-AIV H5 mod | SQ | 22 | 0.2 mL | 0, 14 | 13, 28, 35 |
| 5 | IVP-4: 10 μg HP-AIV H5 mod | IM | 22 | 0.2 mL | 0, 14 | 13, 28, 35 |
| 6 | IVP-5: 60 μg HP-AIV H5 mod | SQ | 22 | 0.2 mL | 0, 14 | 13, 28, 34, 48 |
| 7 | IVP-6: 60 μg HP-AIV H5 mod | IM | 22 | 0.2 mL | 0, 14 | 13, 28, 35 |

[1]MPC—Mock Placebo Control; IVP—Investigational Veterinary Product

0 DA - birds received the first vaccination on day of hatch

TABLE 53

Treatment Descriptions, Two Week Old (14 DA) Birds

| Group ID | Product[1] | Route | # of Birds | Dose | Vaccination, Days | Blood Collection, Days |
|---|---|---|---|---|---|---|
| 9 | PC | SQ | 9 | 0.2 mL | 14, 28 | 27, 42 |
| 10 | IVP-1: 30 μg HP-AIV H5 mod | SQ | 18 | 0.2 mL | 14, 28 | 27, 42 |
| 11 | IVP-2: 30 μg HP-AIV H5 mod | IM | 18 | 0.2 mL | 14, 28 | 27, 42 |

[1]PC—Positive Control; IVP—Investigational Veterinary Product

14DA—a second set of birds received the first vaccination at 14 days post hatch

Results and Conclusions

The 0DA vaccination groups 1-7 were administered the first test article dose on day of hatch (Study Day 0). The same birds received a booster dose of the respective test article on Study Day 14 (see Table 52).

The 14DA vaccination groups (Groups 9-11) were administered the test article on Study Day 14 and treated similarly on Study Day 28 (see Table 53).

TABLE 52

Treatment Descriptions, Day of Age (0 DA) Birds

| Group ID | Product[1] | Route | # of Birds | Dose | Vaccination, Study Days | Blood Collection, Study Days |
|---|---|---|---|---|---|---|
| 1 | MPC: DPBS | SQ | 6 | 0.2 mL | 0, 14 | 13, 28, 35 |
| 2 | IVP-1: 30 μg HP-AIV H5 mod | SQ | 21 | 0.2 mL | 0, 14 | 13, 28, 35 |
| 3 | IVP-2: 30 μg HP-AIV H5 mod | IM | 22 | 0.2 mL | 0, 14 | 13, 28, 35 |
| 4 | IVP-3: 10 μg HP-AIV H5 mod | SQ | 22 | 0.2 mL | 0, 14 | 13, 28, 35 |
| 5 | IVP-4: 10 μg HP-AIV H5 mod | IM | 22 | 0.2 mL | 0, 14 | 13, 28, 35 |
| 6 | IVP-5: 60 μg HP-AIV H5 mod | SQ | 22 | 0.2 mL | 0, 14 | 13, 28, 34, 48 |
| 7 | IVP-6: 60 μg HP-AIV H5 mod | IM | 22 | 0.2 mL | 0, 14 | 13, 28, 35 |

[1]MPC—Mock Placebo Control; IVP—Investigational Veterinary Product

0 DA - birds received the first vaccination on day of hatch

TABLE 53

Treatment Descriptions, Two Week Old (14 DA) Birds

| Group ID | Product[1] | Route | # of Birds | Dose | Vaccination, Days | Blood Collection, Days |
|---|---|---|---|---|---|---|
| 9 | PC | SQ | 9 | 0.2 mL | 14, 28 | 27, 42 |
| 10 | IVP-1: 30 μg HP-AIV H5 mod | SQ | 18 | 0.2 mL | 14, 28 | 27, 42 |
| 11 | IVP-2: 30 μg HP-AIV H5 mod | IM | 18 | 0.2 mL | 14, 28 | 27, 42 |

[1]PC—Positive Control; IVP—Investigational Veterinary Product

14 DA - a second set of birds received the first vaccination at 14 days post hatch On Study Day 27 (13 days post-primary vaccination), serum collected from 14DA birds that received the 30 μg dose via the SQ route (Group 10, IVP-1 30 μg, SQ), showed an 11% seroconversion rate (≥2 HAI) with a GMT of 1.1 (Table 58). A 45% seroconversion rate (≥2 HAI) with a GMT of 1.5 was observed from birds that received 30 μg of pDNA H5 mod via IM route (Group 11, IVP-2 30 μg, IM) (Table 58).

On Study Day 42 (14 days post-boost vaccination), serum collected from 14DA birds that received the 30 μg dose via the SQ route (group 10, IVP-1 30 μg, SQ), showed an 89% seroconversion rate (≥2 HAI) with a GMT of 32.0 (Table 58). A 100% seroconversion rate (≥2 HAI) with a GMT of 60.1 was observed from birds that received 30 μg of pDNA H5 mod via IM route (group 11, IVP-2 30 μg, IM) (Table 58).

TABLE 58

| 14 DA - T10, 30 μg, SQ (IVP-1) and T11, 30 μg, IM (IVP-2) | | | | | |
|---|---|---|---|---|---|
| T10, 30 ug, SQ, IVP-1 | | | T11, 30 ug, IM, IVP-2 | | |
| ID | Day 13 (study day 27) | Day 28 (study day 42) | ID | Day 13 (study day 27) | Day 28 (study day 42) |
| 1201 | <2 | 2 | 1218 | <2 | 16 |
| 1202 | 2 | 256 | 1219 | 4 | 64 |
| 1203 | <2 | <2 | 1221 | 2 | 128 |
| 1204 | <2 | 64 | 1223 | <2 | 64 |
| 1205 | <2 | 128 | 1225 | <2 | 8 |
| 1206 | <2 | 32 | 1226 | 2 | 128 |
| 1207 | <2 | 128 | 1227 | <2 | 256 |
| 1208 | <2 | 128 | 1229 | <2 | 32 |
| 1209 | <2 | 32 | 1231 | 2 | 128 |
| 1210 | <2 | 64 | 1233 | 2 | 128 |
| 1211 | <2 | 32 | 1235 | <2 | 32 |
| 1212 | <2 | 32 | GeoM | 1.5 | 60.1 |
| 1213 | <2 | 32 | % Sero+ | 45 | 100 |
| 1214 | <2 | 32 | % HAI ≥16 | 0 | 91 |
| 1215 | <2 | 128 | | | |
| 1216 | <2 | <2 | | | |
| 1217 | <2 | 32 | | | |
| 1404 | 4 | 64 | | | |
| GeoM | 1.1 | 32.0 | | | |
| % Sero+ | 11 | 89 | | | |
| % HAI ≥16 | 0 | 83 | | | |

Discussion

The vaccine was tested in day of hatch (0DA) and 14 days of age (14DA) birds. Three dose levels were tested in the 0DA birds, 10 μg, 30 μg, and 60 μg of plasmid DNA either IM or SQ. None of the 0DA groups showed detectable levels of antibodies as measured by an HAI assay after one vaccine dose. After the second vaccine dose, all of the groups that received the plasmid, regardless of the dose level, had birds that showed detectable levels of seroconversion. 0DA birds that received the two lower doses, 10 μg and 30 μg, when administered SQ showed low seroconversion rates and low GMTs at all collection times (Tables 57 and 58). However, when the same dose levels were administered IM, seroconversion rates were higher, especially 21 days after the boost vaccination. For the 10 μg dose, 59% of birds were seropositive with a GMT of 5.8 (range 4 to 32, Table 56). For the 30 μg dose, 77% of birds were seropositive with a GMT of 8.8 (ranging from 4 to 64, Table 55). It should be noted that seropositive rates may have been higher if a starting dilution of 2 rather than 4 was used in the HAI assay on all testing days. Serum collected from birds in Groups 6 and 7 that received 60 μg of pDNA H5 mod, IVP-5 60 μg, SQ and IVP-6 60 μg IM, respectively), showed seroconversion rates of 38% with a GMT of 4.1 (34 days post boost vaccination) and 100% with a GMT of 14.1 (14 days post boost vaccination), respectively (Table 57).

On study day 27 (13 days post-primary vaccination), serum collected from 14DA birds in Groups 10 and 11 (30 μg dose at the primary vaccination at 14DA) showed detectable but low antibody levels, to the indicator virus A/gyr-falcon/WA/41088-6/2014 H5N8 with seroconversion rates of 11% and 45% for SQ and IM routes, respectively (Table 58).

On Study Day 42 (14 days post-boost vaccination), serum collected from the 14DA birds that received 30 μg of pDNA H5 mod via the SQ route (Group 10), showed an 89% seroconversion rate (≥2 HAI) with a GMT of 32.0 (Table 58). Samples from birds that received 30 μg of pDNA H5 mod via IM route (Group 11), showed a 100% seroconversion rate (≥2 HAI) with a GMT of 60.1 (Table 58).

The AIV DNA vaccine when formulated at 60 μg/0.2 mL dose with ENABL® LP7 administered IM showed a 100% (22/22) seroconversion rate after two doses in 0DA birds, (range 2-64 HAI) with a GMT of 14.1. Of this group 19/22 birds seroconverted with titers ≥8 HAI and 15/22 with ≥16 HAI (Table 57).

In the older (14DA) birds, 30 μg/0.2 mL dose of Code 1057.D0, administered either IM or SQ showed high rates of seroconversion: 100% (11/11, GMT 60.1, Table 7) and 89% (16/18, GMT 32, Table 58) seroconversion rates respectively, after two doses in 14DA birds. Fifteen of the eighteen (83%) birds receiving the vaccine SQ showed titers ≥32 HAI with a range of 32-256. Ten of the eleven (91%) birds receiving the vaccine IM showed titers ≥16 HAI with a range of 16-256. At the 30 μg dose level, Code 1057.D0 when administered IM in 14 day of age birds fulfills the CVB-stated requirement of ≥90% of birds with a titer ≥16 HAI. When 30 μg was administered SQ, 83% of the SQ birds showed titers of ≥32 HAI.

The serological data of this study supports a reasonable expectation of efficacy for Code 1057.D0 when prepared per the Outline of Production and administered as follows:

60 μg plasmid DNA/dose administered IM in day of age chicks with a booster dose given two weeks later.

30 μg plasmid DNA/dose administered IM or SQ in 14 day old chicks, with a booster dose given two weeks later.

What is claimed is:

1. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof; and wherein the lipophile is present in an amount of about 0.01% to about 5% by volume.

2. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof, wherein the polymer of acrylic or methacrylic acid is present in an amount of about 0.1% to about 3% by volume.

3. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof, wherein the cholesterol is present in an amount of about 0.001% to about 3% by volume.

4. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof, wherein the at least one component is alcohol and the alcohol is present in an amount of from about 0.01% to about 3% by volume.

5. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof, wherein the saponin is present in an amount of about 0.001% to about 0.5% by volume.

6. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof, wherein the adjuvant composition is stable at room temperature and when freeze-dried.

7. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof, further comprising an antigen to thereby form a vaccine composition, wherein the antigen is DNA that is non-replicative competent.

8. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof; further comprising an antigen to thereby form a vaccine composition, wherein antigen is DNA that is non-replicative competent DNA in the form of a plasmid.

9. The adjuvant composition of claim 8, wherein the non-replicative competent DNA in the form of a plasmid is present in the adjuvant composition at an amount of about 10 μg to 30 μg.

10. An adjuvant composition comprising:

a. a lipophile;

b. a cholesterol; and c. a saponin, further comprising at least one component selected from the group consisting of a polymer of acrylic or methacrylic acid, saline, alcohol, sodium hydroxide, and any combination thereof further comprising an antigen to thereby form a vaccine composition, wherein the adjuvant composition is shelf stable at room temperature for at least 18 months.

11. A method of eliciting an immune response comprising the steps of administering a single dose of said antigen in combination with an adjuvant composition selected from the group consisting of claim 1, claim 2, claim 3, claim 4, claim 5, claim 6, claim 7, claim 8, or claim 10 to an animal in need thereof.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Avian influenza virus
<220> FEATURE:
<221> NAME/KEY: MISC_FEATURE
<223> OTHER INFORMATION: Sequence is a HP multibasic cleavage site

<400> SEQUENCE: 1

Pro Leu Arg Glu Arg Arg Arg Lys Arg Gly Leu Phe
1               5                   10